(12) United States Patent
Inoue et al.

US008889617B2

(10) Patent No.: US 8,889,617 B2
(45) Date of Patent: Nov. 18, 2014

(54) LIQUID FOOD COMPOSITION

(75) Inventors: Hiroaki Inoue, Takasago (JP); Yui Kawashima, Takasago (JP); Kazuya Hamada, Takasago (JP); Shinichi Yokota, Takasago (JP); Hiromi Maeda, Osaka (JP); Tatsumasa Mae, Osaka (JP); Jun Tomono, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/516,536

(22) PCT Filed: Dec. 17, 2010

(86) PCT No.: PCT/JP2010/072774
§ 371 (c)(1),
(2), (4) Date: Sep. 12, 2012

(87) PCT Pub. No.: WO2011/074670
PCT Pub. Date: Jun. 23, 2011

(65) Prior Publication Data
US 2013/0172245 A1 Jul. 4, 2013

(30) Foreign Application Priority Data

Dec. 18, 2009 (JP) .................................. 2009-287972

(51) Int. Cl.
*A23L 1/29* (2006.01)
*A61K 9/00* (2006.01)
*A23L 1/308* (2006.01)
*A23L 1/304* (2006.01)
*A23L 1/305* (2006.01)
*A61K 9/10* (2006.01)

(52) U.S. Cl.
CPC ............... *A23L 1/296* (2013.01); *A61K 9/0065* (2013.01); *A23L 1/308* (2013.01); *A23L 1/304* (2013.01); *A61K 9/10* (2013.01); *A23L 1/305* (2013.01)
USPC ................ 514/5.5; 426/656; 426/62; 426/74; 426/654

(58) Field of Classification Search
None
See application file for complete search history.

(56) References Cited

U.S. PATENT DOCUMENTS

2007/0292457 A1 12/2007 Toyama et al.
2008/0160137 A1* 7/2008 Kon et al. ....................... 426/74
2010/0040739 A1 2/2010 Kuribayashi et al.

FOREIGN PATENT DOCUMENTS

| JP | 04-023968 A | 1/1992 |
|---|---|---|
| JP | 2000-169396 A | 6/2000 |
| JP | 2000-169397 A | 6/2000 |
| JP | 2005-513077 A | 5/2005 |
| JP | 2007-503823 A | 3/2007 |
| WO | 03/053165 A1 | 7/2003 |
| WO | 2005/020719 A1 | 3/2005 |
| WO | 2006/041173 A1 | 4/2006 |
| WO | 2008/032432 A1 | 3/2008 |
| WO | 2008/098579 A1 | 8/2008 |

OTHER PUBLICATIONS

Anderson et al. Metabolism Clinical and Experimental. 56;280-288:2007.*
Hasenhuettl, GL. Food Emulsifiers and Their Applications. Chapter 2. 2008.*
Moughal et al. International Dairy Journal. 10;683-690:2000.*
Moughal et al. International Dairy Journal. 10 (2000) 683-690.*
Mondor et al. Journal of Membrane Science. 231 (2004) 169-179.*
Holt et al. The Lancet. 313(8117);636-639:1979.*
Megahed, M. Grasas y Aceites. 50(4);280-282:1999.*
International Search Report of PCT/JP2010/072774, mailing date of Mar. 15, 2011.
Instructions of Ensure Liquid, Abbott Japan Co., Ltd., revised in Jun. of 2012, 13th edition, pp. 1-4 (concise explanation of relevance provided), cited in Offer of Information dated Jul. 9, 2014, from the third party.
An Interview form of Twinline, revised in Dec. of 2008, the 7th edition, pp. 1-40 (concise explanation of relevance provided), cited in Offer of Information dated Jul. 9, 2014, from the third party.

* cited by examiner

*Primary Examiner* — Karlheinz R Skowronek
*Assistant Examiner* — Schuyler Milton
(74) *Attorney, Agent, or Firm* — Westerman, Hattori, Daniels & Adrian, LLP

(57) ABSTRACT

Provided is a liquid food composition capable of semi-solidifying in the stomach, which is a one-pack type product containing a water-soluble dietary fiber preliminarily added thereto and in the form of a liquid that can be easily taken, and stably sustains the liquid nature thereof during distribution and storage. The liquid food composition, which is capable of semi-solidifying in an acidic region, comprises a water-soluble dietary fiber (a), a specific metal compound (b), a protein (c) and an emulsifier (d), and the particle size distribution of particles contained in said liquid food composition shows two or more peaks in a neutral region.

26 Claims, 15 Drawing Sheets

(a)

(b)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

LIQUID FOOD COMPOSITION

TECHNICAL FIELD

The present invention relates to a liquid food composition that is used, for example, by elderly people, people with disease, patients before and after surgery, healthy people, and the like for taking nutrients.

BACKGROUND ART

For elderly people and patients with disease or before and after surgery who cannot take food orally, a tube feeding method is used for nutritional support. The tube feeding method includes a method of administering intravenously nutrition and a method of administering enterally nutrition into the alimentary canal. It is believed that the enteral nutrition is desirably used when the administration to the alimentary canal can be performed because, for example, the enteral nutrition does not require strict aseptic handling and bowel function can be maintained as compared with the intravenous administration. In the enteral nutrition, the administration is often performed through a nasogastric tube, a gastrostomy tube, or the like. For such an administration, liquid nutrition foods are typically used. However, it is known that the use of the liquid nutrition food may cause gastroesophageal reflux disease, aspiration pneumonia, diarrheal disease, leakage from a fistula, or the like because the nutrition food is a liquid. As a measure of such a problem, there are reports that semi-solidification of a nutrition food or a nutrition food having a higher viscosity is effective. However, such measures can not sufficiently solve the problems because, for example, such a food needs a certain amount of time for preparation or a certain amount of force that continues to be applied for pushing out the nutrition food during tube feeding.

As means for solving these problems, there are disclosed, for example, a gelling agent containing a gellan gum and alginic acid and a tube feeding nutrition food containing the gelling agent (Patent Document 1) as well as an enteral nutrient using carrageenan in sodium form as a semi-solidifying agent (Patent Document 2). These inventions intend to prevent the problems by adding, to a liquid food, the gellan gum, the carrageenan, or the like for gelation (semi-solidification) of the liquid food. These gelation techniques for liquid foods are considered to be also effective for the relief of the feeling of hunger, the suppression of sudden increase in blood glucose level, and the like and inventions relating to the applications of such a technique to a diet food and a food for diabetes are also disclosed (Patent Documents 3 to 5).

However, it is supposed that there is still room for improvement in these conventional gelation techniques for liquid foods from the viewpoints of the change in physical properties due to dilution of food, easiness in food intake, stability of food during storage, a nutritional viewpoint of food, and the like. For example, in the tube feeding nutrition food disclosed in Patent Document 1, a gelling agent simultaneously containing a gellan gum and alginic acid is added to a tube feeding nutrition food. However, after the gelling agent is added to the tube feeding nutrition food, water is required to be further added, and such preparation takes some time and effort. In addition, the food after preparation is diluted by the amount of the gelling agent added and hence may have greatly altered physical properties from those of the original tube feeding nutrition food. In Patent Document 2, carrageenan is added to a food as a semi-solidifying agent, and the food is semi-solidified in a short period after preparation. Thus, even when a prepared food has flowability capable of tube feeding, it requires a certain amount of force for passing through a tube because it has a high viscosity and may cause tube clogging. Hence, such a food is not necessarily easily taken. Furthermore, in these techniques (Patent Documents 1 and 2), when the gelling agent or the semi-solidifying agent is preliminarily mixed in a food, the food is solidified with time. Thus, the gelling agent such as a water-soluble dietary fiber is added to a food immediately before intake. Therefore, the techniques are a technique in which two liquids are mixed for use and do not provide a one-pack type product in which a gelling agent is preliminarily mixed in a food.

Patent Document 3 discloses a technique relating to a diet food and a food for diabetes utilizing that a simple composition composed of alginic acid and a calcium compound insoluble in a neutral condition changes into a gel when the composition is in contact with gastric juice. However, the water-soluble dietary fiber such as alginic acid may cause component separation such as phase separation when such a fiber is mixed with protein. No protein is actually mixed in Patent Document 3. The technique in Patent Document 3 is a technique for providing a diet food and a food for diabetes. There is no description relating to a method for adding mineral components other than a calcium compound and the effect is not studied. However, mineral components other than a calcium compound are important mineral components for humans and a composition without mineral components other than the calcium compound is not a nutritionally satisfactory composition. Furthermore, the technique disclosed in Patent Document 3 may cause problems. For example, in the preparation of an enteral nutrition food that is taken by, for example, elderly people and patients with disease or before and after surgery who cannot take food orally or of a nutrition food containing many components such as protein and mineral components, physical properties may be impaired during preparation or storage and nutrient components may be separated during storage.

Patent Document 4 relates to a composition that is liquid at around neutral pH and that forms an adhesive matrix at low pH. The composition includes (a) at least 0.05 wt % of pectin having a degree of methoxylation of 2 to 50 and/or of alginate, (b) at least 5 mg of calcium per 100 ml, and (c) at least 0.1 wt % of indigestible oligosaccharide having a degree of polymerization of 2 to 60 as essential components and includes digestible carbohydrates, lipids, and plant proteins such as a soybean as optional components. Patent Document 5 relates to a food composition having enhanced satiety effect. The food composition includes at least 1 wt % of protein and 0.1 to 5 wt % of a biopolymer thickening agent (for example, pectin and alginate) that is not denatured or hydrolyzed between pH 2 and 4 as essential components. The food compositions described in these patents have an effect of obtaining higher viscosity in the stomach to enhance satiety effect. However, the present inventors have studied to reveal that a food composition prepared by mixing raw materials described in these patents causes problems of generating aggregates during preparation and/or storage. When such aggregates have been generated, tube feeding of the prepared composition has caused a problem of tube clogging due to the aggregates present in the liquid food composition (especially a throttle for controlling feeding speed has been clogged with the aggregates). Furthermore, the liquid food composition has obtained a high viscosity due to the presence of the aggregates to result in poor tube passage performance of the liquid food composition. Moreover, for oral intake of the prepared composition, the presence of the aggregates has increased "granular texture" and the presence of the aggregates has increased the viscosity to greatly impair "swallowing feeling". Therefore, the conventional liquid food composition that is semi-solidified in an acidic region has been very difficult to be used.

CITATION LIST

Patent Literatures

Patent Document 1: JP-A No. 2000-169396

Patent Document 2: International Publication WO 2006/041173

Patent Document 3: JP-A No. 4-23968

Patent Document 4: JP-A No. 2005-513077

Patent Document 5: JP-A No. 2007-503823

SUMMARY OF INVENTION

Technical Problem

As described above, the conventional gelation technique for liquid foods is insufficient from the viewpoints of the change in physical properties of food due to the dilution of food, easiness in food intake, stability of food during storage, and the like and there is a demand for a more satisfactory liquid food composition.

In view of the above circumstances, it is an object of the present invention to provide a liquid food composition that is semi-solidified in the stomach and preliminarily contains a water-soluble dietary fiber and that is in the form of a liquid, is easily taken, stably sustains the liquid nature of the composition during preparation and even during distribution and storage, and also, is unlikely to cause clogging in a tube and has good tube passage performance at the time of tube feeding, has less "granular texture" and good "swallowing feeling" at the time of oral intake, and is consequently easily taken.

Solution to Problem

In order to solve the problems, the present inventors have carried out intensive studies, for example, on the selection of components in a food. As a result, the inventors have found that by mixing a water-soluble dietary fiber such as alginic acid and a salt thereof, a metal compound containing a necessary mineral component for humans and not causing gelation of the water-soluble dietary fiber in a neutral region, such as a calcium compound having poor solubility and a magnesium compound having poor solubility, a plant protein such as a soybean protein and a hydrolysate thereof, and an emulsifier such as lysolecithin and sucrose laurate and by controlling the particle size distribution of a liquid food composition containing these components, a liquid food composition that is semi-solidified in an acidic condition in the stomach can be provided and the liquid food composition is (1) a composition preliminarily containing the water-soluble dietary fiber, (2) in the form of a liquid and is easily taken, (3) stably sustains the liquid nature even during distribution and storage, (4) does not generate aggregates, and (5) can satisfy nutritional requirements, and the present invention has been accomplished.

That is, the present invention relates to (1) a liquid food composition being semi-solidified in an acidic region, the liquid food composition comprising
a water-soluble dietary fiber (a),
a metal compound (b) containing a necessary mineral component for humans and not causing gelation of the water-soluble dietary fiber in a neutral region,
a protein (c), and
an emulsifier (d),
the liquid food composition including particles having a particle size distribution with two or more peaks in the neutral region;

(2) the liquid food composition according to the item (1), in which the liquid food composition in a semi-solidified state has a viscosity of 1,000 cP or more in the acidic region;

(3) the liquid food composition according to the item (2), in which at least one of two or more peaks present in the particle size distribution of the particles is present at a particle size of 3,000 nm or smaller;

(4) the liquid food composition according to any one of the items (1) to (3), in which ultrasonic treatment of the liquid food composition increases a frequency of the at least one peak present at a particle size of 3,000 nm or smaller after the ultrasonic treatment as compared with that before the ultrasonic treatment and reduces a frequency of at least one peak other than the peak having the increased frequency after the ultrasonic treatment as compared with that before the ultrasonic treatment;

(5) the liquid food composition according to any one of the items (1) to (4), in which, in the at least one peak having the increased frequency in the particle size distribution of particles after the ultrasonic treatment, the increased frequency is 105% or more with respect to the frequency in the particle size distribution of particles before the ultrasonic treatment and, in the at least one peak having the reduced frequency in the particle size distribution of particles after the ultrasonic treatment, the reduced frequency is 60% or less with respect to the frequency in the particle size distribution of particles before the ultrasonic treatment;

(6) a liquid food composition being semi-solidified in an acidic region, the liquid food composition comprising
a water-soluble dietary fiber (a),
a metal compound (b) containing a necessary mineral component for humans and not causing gelation of the water-soluble dietary fiber in a neutral region,
a protein (c), and
an emulsifier (d),
the liquid food composition having a distribution curve of two or more inflection points, when representing a particle size distribution of particles included in the liquid food composition in the neutral region, as a distribution curve of a passing particle integrated value based on volume;

(7) the liquid food composition according to the item (6), in which the liquid food composition in a semi-solidified state has a viscosity of 1,000 cP or more in the acidic region;

(8) the liquid food composition according to the item (7), in which at least one of the inflection points in the distribution curve is present in a particle size section having a particle size of 3,000 nm or smaller;

(9) the liquid food composition according to any one of the items (6) to (8), in which at least one of the inflection points in the distribution curve is present in a particle size section having a particle size of 2,000 nm or smaller, and ultrasonic treatment of the liquid food composition increases a passing particle integrated value corresponding to the at least one inflection point, present in a particle size section having a particle size of 2,000 nm or smaller, by 5% or more after the ultrasonic treatment as compared with that before the ultrasonic treatment;

(10) the liquid food composition according to any one of the items (6) to (9), in which at least one of the inflection points in the distribution curve is present in a particle size section having a particle size of 2,000 nm or smaller, and ultrasonic treatment of the liquid food composition shifts a passing particle integrated value corresponding to the at least one inflection point, present in a particle size section having a particle size of 2,000 nm or smaller, to a section having a passing particle integrated value of 25% or more after the ultrasonic treatment as compared with that before the ultrasonic treatment;

(11) the liquid food composition according to any one of the items (1) to (10), in which aggregate weight determined by a measurement method below is 0.1 g or less, aggregate weight: 200 ml of the liquid food composition is filtered using a 264-mesh nylon screen of which dry weight (W1) is preliminarily weighed; the nylon screen after the filtration is dried at 60° C. for 1 hour and then cooled; a dry weight (W2) of the screen is weighed; and difference (W2−W1) between the dry weights before and after the filtration is calculated to determine weight of an aggregate obtained as a residue;

(12) the liquid food composition according to any one of the items (1) to (11), in which the water-soluble dietary fiber (a) is alginic acid and/or a salt thereof;

(13) the liquid food composition according to any one of the items (1) to (12), in which the protein (c) is a plant protein derived from a plant;

(14) the liquid food composition according to the item (13), in which the plant protein is a bean-derived protein;

(15) the liquid food composition according to the item (14), in which the bean-derived protein is a soybean protein and/or a hydrolysate thereof;

(16) the liquid food composition according to any one of the items (1) to (15), in which the metal compound (b) containing a necessary mineral component for humans and not causing gelation of the water-soluble dietary fiber in the neutral region is at least one compound selected from the group consisting of a metal compound having poor solubility in the neutral region, a metal compound included in a microorganism such as a yeast, and a metal compound included in a microcapsule;

(17) the liquid food composition according to the item (16), in which the metal compound (b) containing a necessary mineral component for humans and not causing gelation of the water-soluble dietary fiber (a) in the neutral region is a calcium compound having poor solubility in the neutral region and/or a magnesium compound having poor solubility in the neutral region;

(18) the liquid food composition according to the item (17), in which the calcium compound (b) having poor solubility in the neutral region is at least one compound selected from the group consisting of calcium citrate, calcium carbonate, calcium dihydrogen pyrophosphate, tricalcium phosphate, calcium monohydrogen phosphate, calcium stearate, and calcium silicate;

(19) the liquid food composition according to the item (17), in which the magnesium compound (b) having poor solubility in the neutral region is at least one compound selected from the group consisting of magnesium carbonate, magnesium oxide, magnesium stearate, and trimagnesium phosphate;

(20) the liquid food composition according to the item (16), in which the metal compound (b) containing a necessary mineral component for humans and not causing gelation of the water-soluble dietary fiber (a) in the neutral region is at least one selected from the group consisting of a zinc-containing yeast, a copper-containing yeast, a manganese-containing yeast, a chromium-containing yeast, a selenium-containing yeast, and a molybdenum-containing yeast;

(21) the liquid food composition according to the item (16), in which the metal compound (b) containing a necessary mineral component for humans and not causing gelation of the water-soluble dietary fiber (a) in the neutral region is ferric sodium citrate;

(22) the liquid food composition according to any one of the items (1) to (21), in which the emulsifier (d) is an emulsifier having an HLB value of more than 9;

(23) the liquid food composition according to the item (22), in which the emulsifier (d) is lysolecithin and/or a sucrose fatty acid ester composed of a fatty acid monoester having a carbon number of 18 or less;

(24) the liquid food composition according to the item (22) or (23), in which the emulsifier (d) is lysolecithin and/or sucrose laurate;

(25) the liquid food composition according to any one of the items (1) to (24), further including a fat (e);

(26) the liquid crystal food composition according to the item (25), in which the emulsifier (d) and the fat (e) are mixed in a ratio ((d)/(e), based on weight) of more than 5/100 and 30/100 or less;

(27) the liquid food composition according to any one of the items (1) to (26), in which at least the components (a) to (d) are filled in a container as a one-pack type product;

(28) the liquid food composition according to any one of the items (1) to (27), further including a nutrient component (f);

(29) the liquid food composition according to any one of the items (1) to (28), sustaining a liquid state during storage;

(30) the liquid food composition according to any one of the items (1) to (29), in which the liquid food composition is semi-solidified in an acidic environment in a stomach and has an effect of preventing gastroesophageal reflux disease, aspiration pneumonia, diarrheal disease, leakage from a fistula, or the like;

(31) the liquid food composition according to any one of the items (1) to (30), in which the liquid food composition is semi-solidified in an acidic environment in a stomach and has an effect of relieving the feeling of hunger;

(32) the liquid food composition according to any one of the items (1) to (31), in which the liquid food composition is semi-solidified in an acidic environment in a stomach and has an effect of suppressing sudden increase in blood glucose level;

(33) an enteral nutrition food including the liquid food composition according to any one of the items (1) to (32);

(34) an oral nutrition food including the liquid food composition according to any one of the items (1) to (32); and

(35) a diet food including the liquid food composition according to any one of the items (1) to (32).

Advantageous Effects of Invention

The liquid food composition that is semi-solidified in an acidic condition of the present invention as described above preliminarily includes a water-soluble dietary fiber and hence eliminates the time and effort for adding a gelling agent and the like at the time of intake. In addition, the liquid food composition can be easily taken because it is liquid. The liquid food composition of the present invention can stably sustain quality of the composition during preparation and even during distribution and storage for a long time, and hence the liquid food composition that is semi-solidified in an acidic condition can be practically supplied. The present invention can also provide a novel liquid food composition that has a nutritionally satisfactory formulation by containing, for example, necessary mineral components for humans, such as calcium, and a plant protein such as a soybean protein while providing the advantages above. In particular, the liquid food composition can suppress the generation of aggregates during preparation and/or storage of the composition. Therefore, the present invention can provide a liquid food composition that is unlikely to cause clogging in a tube and has good tube passage performance at the time of tube feeding, has less "granular texture" and good "swallowing feeling" at the time of oral intake, and is consequently easily taken.

The liquid food composition according to the present invention can be used for an enteral nutrition food and an oral nutrition food by taking the advantages and can be used for, for example, a nutrition food, an enteral nutrition food, an enteral nutrient including a diet classified as a medicinal supplies, an elemental diet, a polymeric formula, an oligomeric formula, a high density liquid diet, a diet food, and a food for diabetes.

DESCRIPTION OF EMBODIMENTS

Figure 1:
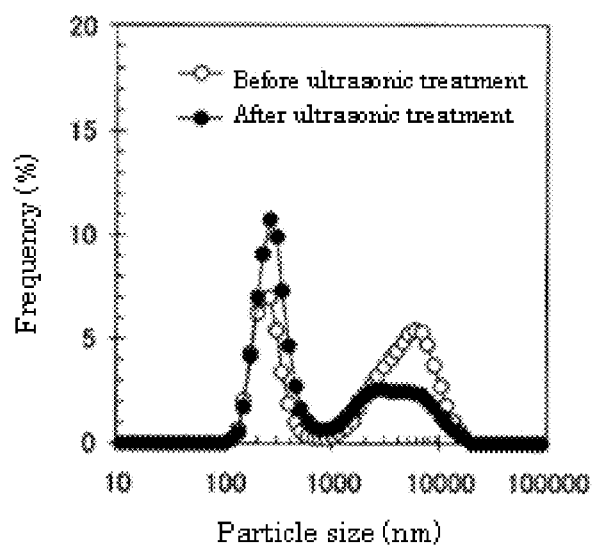
FIG. 1($a$) is a figure showing the particle size distribution of particles in a liquid food composition of Example 1 and FIG. 1($b$) is a figure showing the particle size distribution of particles in the liquid food composition of Example 1 as a distribution curve where vertical axis is passing particle integrated value (%) based on volume.
Figure 1:
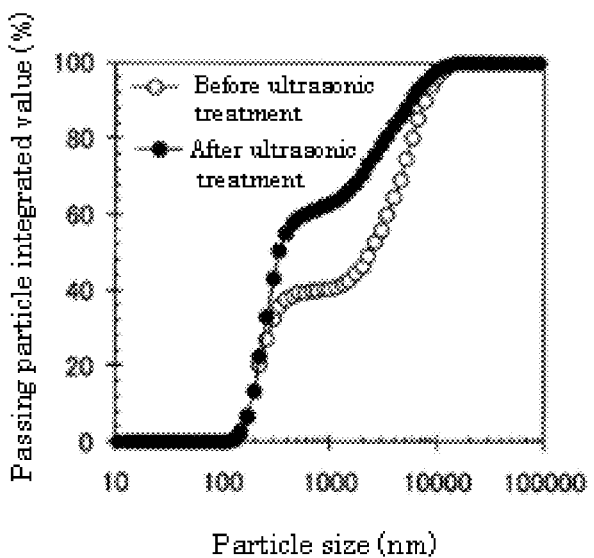

Hereinafter, the present invention will be described in detail.

The liquid food composition of the present invention includes a water-soluble dietary fiber (a), a metal compound (b) containing a necessary mineral component for humans and not causing gelation of the water-soluble dietary fiber in a neutral region, a protein (c), and an emulsifier (d) and is semi-solidified in an acidic region, and the liquid food composition is characterized by containing particles having a particle size distribution with two or more peaks in a neutral region.

The "semi-solidification" in the present invention is a state in which the liquid nature of the liquid food composition is changed and means insolubilization, increase in viscosity, solation, gelation, and the like of components in the composition. The state is not specifically limited as long as the liquid nature at the time of intake is changed by an acidic condition in the stomach. The semi-solidification can also be represented by the solidification ratio described later. In the present invention, the solidification ratio is not particularly limited but is preferably 45% or more. A liquid food composition having a solidification ratio of 45% or more is more semi-solidified in an acidic region in the stomach and consequently can more effectively provide, for example, the prevention effect of gastroesophageal reflux disease, aspiration pneumonia, diarrheal disease, leakage from a fistula, and the like, the relief of the feeling of hunger, and the suppression effect of sudden increase in blood glucose level.

As the index for semi-solidification, viscosity can be also used. The viscosity when the liquid food composition is semi-solidified is not particularly limited as long as gastroesophageal reflux can be prevented and a feeling of satiety is enhanced, but the viscosity when the liquid food composition is semi-solidified is preferably 1,000 cP or more, more preferably 2,000 cP or more, even more preferably 5,000 cP or more, and specifically preferably 10,000 cP or more. A semi-solidified liquid food composition having a viscosity of 1,000 cP or more can more effectively provide, for example, the prevention effect of gastroesophageal reflux disease, aspiration pneumonia, diarrheal disease, leakage from a fistula, and the like, the relief of the feeling of hunger, and the suppression effect of sudden increase in blood glucose level.

In the present invention, the "liquid nature of a liquid food composition" means a nature by which easiness in intake of the liquid food composition is not impaired and means, for example, that there is no solid (for example, aggregate) causing tube clogging and the composition is in a uniform state. Here, the "uniform state" means that components are little separated and the product quality is good. A liquid food composition in which components are largely separated has poor appearance even when there is no solid (for example, aggregate) causing tube clogging. The poor appearance reduces the commercial value and such a liquid food composition may not accepted in the market. The liquid food composition of the present invention undergoes little change in physical properties such as solidification and separation of components even during storage for a long time and can sustain the "liquid nature" for a long time.

The water-soluble dietary fiber (a) usable in the present invention is not particularly limited as long as the liquid nature of the liquid food composition is not impaired at the time of intake and during storage and the liquid food composition can be semi-solidified in an acidic region. Usable examples of the water-soluble dietary fiber (a) include alginic acid and/or a salt thereof, gellan gum, pectin, carrageenan, curdlan, and polyglutamic acid. Among them, alginic acid and/or a salt thereof are particularly preferably used.

The type of alginic acid and/or a salt thereof is not particularly limited and products meeting standards for pharmaceutical excipients or standards for food additives can be used. The type of a salt of alginic acid is not particularly limited but a sodium salt, a potassium salt, and an ammonium salt are especially preferred. From the viewpoint that the flowability in a neutral region is suppressed to low viscosity, the alginic acid and the salt thereof preferably has a viscosity of 500 cP or less, more preferably 300 cP or less, even more preferably 100 cP or less, and specifically preferably 50 cP or less, in a 1 wt % aqueous solution (20° C.). In the present invention, the adequate concentration of the water-soluble dietary fiber (a) such as alginic acid and/or a salt thereof (hereinafter, also collectively referred to as "alginic acid") varies depending on a type of the water-soluble dietary fiber and a formulation of the composition, but from the viewpoint of further acceleration of the semi-solidification of the liquid food composition in an acidic region, the concentration is principally 0.3 wt % or more, preferably 0.5 wt % or more, more preferably 0.7 wt % or more, and even more preferably 1.0 wt % or more, in the liquid food composition. A water-soluble dietary fiber having a concentration of less than 0.3 wt % may lead to insufficient semi-solidification of the liquid food composition in an acidic region. The upper limit of the concentration of the water-soluble dietary fiber such as alginic acid is preferably 5.0 wt % or less, more preferably 2.5 wt % or less, even more preferably 2.0 wt % or less, and most preferably 1.5 wt % or less, in the liquid food composition. A water-soluble dietary fiber having a concentration of more than 5.0 wt % increases the viscosity of the liquid food composition, and consequently the easiness in intake may be impaired.

The pH of the liquid food composition of the present invention is not particularly limited as long as the liquid nature of the liquid food composition is not impaired at the time of intake and during storage, but the liquid food composition principally preferably has a pH of more than 5.5, more preferably a pH of 6.0 or more, and even more preferably a pH of 6.5 or more. A liquid food composition having a pH of 5.5 or less may lead to semi-solidification of the water-soluble dietary fiber in the composition and may not sustain the liquid nature at the time of intake and during storage. The upper limit of pH of the liquid food composition is also not particularly limited, but the liquid food composition principally preferably has a pH of 10.0 or less, more preferably a pH of 9.0 or less, and even more preferably a pH of 8.0 or less. A liquid food composition having a pH of more than 10.0 may lead to degradation of the water-soluble dietary fiber in the composition and may result in insufficient semi-solidification of the liquid food composition in an acidic region. The lower limit of the neutral region in the present invention is preferably a pH of more than 5.5, more preferably a pH of 6.0, and even more preferably a pH of 6.5. The upper limit of the neutral region is preferably a pH of 10.0 or less, more preferably a pH of 9.0 or less, and even more preferably a pH of 8.0. The acidic region in the present invention has a pH of 5.5 or less, preferably a pH of 4.5 or less, and more preferably a pH of 3.5 or less.

The term "not causing gelation of the water-soluble dietary fiber" in the present invention means a compound that does not impair the liquid nature of the liquid composition even when the compound is mixed with a water-soluble dietary fiber (a) in a container and, for example, reacted with the water-soluble dietary fiber (a). In other words, when the liquid nature of the composition is not impaired by mixing of a compound that has any characteristic or is in any state or in any amount, such a compound is regarded as a compound "not causing gelation of the water-soluble dietary fiber". Accordingly, in the present invention, the metal compound (b) not causing gelation of the water-soluble dietary fiber in a neutral region is not limited to a metal compound intrinsically having characteristics of not causing gelation of the water-soluble dietary fiber in a neutral region. Even a metal compound causing gelation of the water-soluble dietary fiber in a neutral region can be used, if the compound is in any state that does not cause gelation of the water-soluble dietary fiber in a neutral region or is in any amount that does not cause gelation of the water-soluble dietary fiber in a neutral region.

The "necessary mineral component for humans" in the present invention means essential minerals for humans, and examples of the mineral component include sodium, potassium, calcium, magnesium, iron, zinc, copper, manganese, iodine, selenium, chromium, and molybdenum. Other examples include phosphorus, sulfur, and cobalt that are considered as essential minerals, and these minerals may be used in combination. However, it is preferably that such a compound has characteristics and used in a state or an amount that does not impair the liquid nature of the liquid food composition. Examples of the metal compound (b) that is usable in the present invention, contains a necessary mineral component for humans, and does not cause gelation of the water-soluble dietary fiber in a neutral region include an alkali metal compound such as a sodium compound and a potassium compound; an alkaline earth metal compound such as a calcium compound and a magnesium compound; and other compounds of a metal such as chromium, molybdenum, manganese, iron, copper, zinc, and selenium. These metal compounds may be in any state as long as the gelation of the water-soluble dietary fiber is not caused when a food composition containing such a metal compound is in a neutral region, but such a metal compound is preferably, for example, in the state of a metal salt having poor solubility in a neutral region, in the state contained in a microorganism such as a yeast, or in the state contained in a microcapsule that has poor solubility in a neutral region and is dissolved in an acidic region.

As the metal compound (b) not causing gelation of the water-soluble dietary fiber in a neutral region, even a metal compound intrinsically causing gelation of the water-soluble dietary fiber due to its characteristics and state can be used as long as the liquid nature of the liquid food composition is not impaired at the time of intake and during storage, for example, in an amount that is too small in the liquid food composition.

Among the metal compounds not causing gelation of the water-soluble dietary fiber in a neutral region, a calcium compound and a magnesium compound are preferred because such compounds are a useful mineral component. The calcium compound and the magnesium compound may have any state as long as the gelation of the water-soluble dietary fiber is not caused in a neutral region. Among them, a calcium compound having poor solubility in a neutral region and a magnesium compound having poor solubility in a neutral region are preferably used. Essential amounts of calcium and magnesium are higher than those of other mineral components in humans. Thus, the calcium compound having poor solubility and the magnesium compound having poor solubility are preferably used rather than the state contained in a yeast and the like.

A preferred calcium compound usable in the present invention is not particularly limited as long as it has poor solubility in a neutral region and has a solubility at which the liquid nature of the liquid food composition is not impaired at the time of intake and during storage by the reaction with the water-soluble dietary fiber contained in the composition. For example, calcium citrate, calcium carbonate, calcium dihydrogen pyrophosphate, tricalcium phosphate, calcium monohydrogen phosphate, calcium stearate, and calcium silicate are preferably used. Among them, calcium carbonate, calcium dihydrogen pyrophosphate, and tricalcium phosphate are preferably used. Among these calcium compounds, calcium carbonate and tricalcium phosphate are more preferably used due to especially low solubility. These calcium compounds may be used alone or in combination of two or more of them.

A preferred magnesium compound usable in the present invention is not also particularly limited as long as it has poor solubility in a neutral region and has a solubility at which the liquid nature of the liquid food composition is not impaired at the time of intake and during storage by the reaction with the water-soluble dietary fiber contained in the composition. For example, magnesium carbonate, magnesium oxide, magnesium stearate, trimagnesium phosphate, and magnesium silicate are preferably used. Among them, magnesium carbonate and magnesium oxide that have poor solubility among magnesium compounds usable as food additives are more preferably used. These magnesium compounds may be used alone or in combination of two or more of them.

For the calcium compound and the magnesium compound, any of the above compounds may be used and the combination is not also particularly limited, but as a combination that has suitable solubility in a neutral region and that is suitably used for a food, a combination of calcium carbonate and magnesium carbonate is especially preferred. Each amount in the food composition is not particularly limited as long as it is a nutritionally satisfactory amount for a person taking the liquid food composition and is a sufficient amount for the semi-solidification of the liquid food composition in an acidic region, but the amount of calcium is 0 µg/100 ml, 1 µg/100 ml or more, preferably 1 mg/100 ml or more, more preferably 10 mg/100 ml or more, even more preferably 30 mg/100 ml or more, furthermore preferably 50 mg/100 ml or more, and particularly preferably 75 mg/100 ml or more, in terms of calcium. The upper limit of the calcium amount is not particularly limited, but is 3,000 mg/100 ml or less, preferably 2,000 mg/100 ml or less, more preferably 1,000 mg/100 ml or less, even more preferably 500 mg/100 ml or less, and furthermore preferably 250 mg/100 ml or less. The amount of magnesium is 0 µg/100 ml, 1 µg/100 ml or more, preferably 1 mg/100 ml or more, more preferably 10 mg/100 ml or more, even more preferably 15 mg/100 ml or more, furthermore preferably 20 mg/100 ml or more, and particularly preferably 35 mg/100 ml or more, in terms of magnesium. The upper limit of the magnesium amount is not particularly limited, but is 500 mg/100 ml or less, preferably 350 mg/100 ml or less, more preferably 100 mg/100 ml or less, even more preferably 75 mg/100 ml or less, and furthermore preferably 50 mg/100 ml or less.

The metal compound (b) may suitably include the calcium compound, the magnesium compound, and one or more compounds of the various metal compounds described in the paragraph [0023] in a nutritionally satisfactory amount for, for example, a person taking or administering the liquid food composition. The total amount of the metal compounds (b) is principally about 1 µg to 5 mg/100 ml, preferably about 1 µg to 50 mg/100 ml, more preferably about 1 µg to 100 mg/100 ml, even more preferably about 1 µg to 500 mg/100 ml, and furthermore preferably about 1 µg to 1000 mg/100 ml.

The protein (c) used in the present invention is not particularly limited, and usable examples of the protein include a plant protein such as a soybean protein, a wheat protein, a pea protein, and a rice protein and/or a hydrolysate of such a protein. However, a protein causing gelation of the dietary fiber in a neutral region is excluded. Among these proteins, a soybean protein and/or a hydrolysate thereof are preferred. By mixing such a protein, the liquid nature of the liquid food composition can be stably sustained during preparation and even during distribution and storage. The type of the soybean protein is not particularly limited and usable examples of the soybean protein include a soy milk, a concentrated soybean protein, an isolated soybean protein, and a soybean peptide. The amount of the protein is not particularly defined and is preferably a nutritionally satisfactory amount for a person taking or administering the liquid food composition. The amount is 0.3 g/100 ml or more, more preferably 1.0 g/100 ml or more, even more preferably 2.0 g/100 ml or more, and particularly preferably 4.0 g/100 ml or more. The upper limit of the protein amount is principally 10.0 g/100 ml or less, more preferably 7.5 g/100 ml or less, and particularly preferably 5.0 g/100 ml or less because such a range is suitable for achieving the stability of the liquid food composition as the feature of the present invention. From the viewpoint of ensuring the flowability in a neutral region, a protein material preferably contains Ca in an amount of 2.0% or less, more preferably 1.5% or less, furthermore preferably 1.0% or less, and particularly preferably 0.8% or less.

The emulsifier (d) usable in the present invention is not particularly limited. From the viewpoint of suppressing the generation of aggregates, examples of the emulsifier include lysolecithin and a sucrose fatty acid ester. As the lysolecithin, that derived from soybean or egg yolk can be used, and the lysolecithin derived from soybean is preferably used. Any of a crude lysolecithin, a purified lysolecithin, a fractionated lysolecithin, and an enzyme-modified lysolecithin may be used, and the purified lysolecithin or the fractionated lysolecithin is preferably used. The sucrose fatty acid ester is not particularly limited. A preferred sucrose fatty acid ester includes, as a main component, a monoester composed of a fatty acid residue having a carbon number of 18 or less, preferably 16 or less, more preferably 14 or less, and even more preferably 12 or less. Among them, a more preferred sucrose fatty acid ester includes, as a main component, a monoester with lauric acid specifically having a carbon number of 12 or less. These emulsifiers may be used alone and in combination of two or more of them.

The emulsifier (d) usable in the present invention can be selected with reference to HLB (hydrophile-lipophile balance) value of an emulsifier. From the viewpoint of suppressing the generation of aggregates, a preferably used emulsifier has an HLB value of more than 9, preferably 10 or more, and more preferably 12 or more. Examples of the emulsifier having an HLB value of more than 9 include the lysolecithin (such as SLP-PasteLyso, SLP-WhiteLyso, and SLP-LPC70 manufactured by Tsuji Oil Mills Co., Ltd.) having an HLB value of about 12 and a sucrose fatty acid ester having an HLB value of more than 9, such as a sucrose stearate (S-970, S-1170, S-1570, and S-1670), a sucrose palmitate (P-1570 and P-1670), sucrose myristate (M-1695), sucrose oleate (O-1570), and a sucrose laurate (L-1695), manufactured by Mitsubishi-Kagaku Foods Corporation. Among them, lysolecithin and sucrose laurate are preferably used.

The adequate concentration of the emulsifier (d) in the liquid food composition varies depending on the formulation of the composition, but the concentration in the liquid food composition is principally preferably more than 0.17 wt % (when a fat is added, more than 5 wt % with respect to the fat), more preferably 0.24 wt % or more (when a fat is added, 7 wt % or more with respect to the fat), and even more preferably 0.34 wt % or more (when a fat is added, 10 wt % or more with respect to the fat). A liquid food composition containing the emulsifier in an amount of 0.17 wt % or less is unlikely to suppress the generation of aggregates. The upper limit is not particularly limited, but the addition of the emulsifier in an excess amount leads to the increase in the viscosity. Hence, the upper limit is 1.02 wt % or less (when a fat is added, 30 wt % or less with respect to the fat), preferably 0.85 wt % or less (when a fat is added, 25 wt % or less with respect to the fat), more preferably 0.68 wt % or less (when a fat is added, 20 wt % or less with respect to the fat), and even more preferably 0.51 wt % or less (when a fat is added, 15 wt % or less with respect to the fat).

The fat (e) usable in the present invention is not particularly limited and usable examples of the fat include a natural fat such as a soybean oil, a corn oil, a rape seed oil, a palm oil, a palm kernel oil, a safflower oil, an olive oil, a perilla oil, a fish oil, a beef tallow, and a lard; as well as a medium chain fatty acid triglyceride; a saturated fatty acid such as stearic acid; an unsaturated fatty acid such as oleic acid, α-linolenic acid, γ-linolenic acid, linoleic acid, eicosapentaenoic acid, docosahexaenoic acid, and arachidonic acid; and a combination of them. The amount of the fat (e) in the liquid food composition is not particularly limited and the adequate amount varies depending on the formulation of the composition, but the amount is preferably a nutritionally satisfactory amount for a person taking or administering the liquid food composition. Hence, the amount is about 0 g/100 ml, preferably about 0.2 g/100 ml or more, more preferably about 0.5 g/100 ml or more, even more preferably about 1.0 g/100 ml or more, furthermore preferably about 2.0 g/100 ml or more, particularly preferably about 3.0 g/100 ml or more, and particularly more preferably about 3.4 g/100 ml or more. The upper limit of the amount of the fat is principally 10.0 g/100 ml or less, preferably 7.5 g/100 ml or less, more preferably 5.0 g/100 ml or less, and particularly preferably 4.0 g/100 ml or less because a formulation in such a range is preferred from the viewpoint of suppressing the generation of aggregates.

The amount of the emulsifier (d) can be controlled depending on the amount of a fat in the composition. The emulsifier (d) and the fat (e) are mixed in a ratio ((d)/(e), based on weight) of more than 5/100, preferably 7/100 or more, and more preferably 10/100 or more. A composition having a ratio of 5/100 or less is unlikely to suppress the generation of aggregates. The upper limit is not particularly limited, but in order not to increase the viscosity of the composition, the upper limit is 30/100 or less, preferably 25/100 or less, more preferably 20/100 or less, and furthermore preferably 15/100 or less.

In the present invention, a nutrient component (f) other than the above components may be included. In the present invention, a composition by which, for example, a person taking or administering the liquid food composition can achieve intended nutritional support or nutrition control is referred to as a "nutritionally satisfactory liquid food composition". The nutrient component capable of being included in the liquid food composition is not particularly limited as long as intended nutritional support or nutrition control can be achieved. As described above, in the present invention, the liquid food composition includes the water-soluble dietary fiber (a), the metal compound (b) containing a necessary mineral component for humans, and the protein (c) as a nitrogen source, such as a soybean protein and a hydrolysate thereof and results in a nutritionally satisfactory liquid food composition. As the metal compound (b) containing a necessary mineral component for humans, a compound not causing gelation of the water-soluble dietary fiber (a) in a neutral region is preferably used. The use of a compound other than such a compound may cause a reaction with the water-soluble dietary fiber in the composition, and consequently may impair the liquid nature of the liquid food composition during storage. As the protein as a nitrogen source, an animal protein may be contained in addition to the plant protein such as a soybean protein and all nitrogen sources are not necessarily derived from a plant protein such as a soybean protein. For example, a common protein such as a milk protein, sodium caseinate, and an egg protein as well as a peptide and hydrolysate derived from such a protein may be properly used in combination as a nitrogen source. Furthermore, for the nitrogen source, for example, various amino acids such as an essential amino acid may also be used. However, such a compound is preferably used within characteristics, a state, and an amount not impairing the liquid nature of the liquid food composition.

For the nutrient component (f) other than the above components, any material may be used as long as the liquid nature of the liquid food composition is not impaired at the time of intake and during storage and a nutritionally satisfactory component for a person taking the liquid food composition may be appropriately added. Examples of carbohydrates include starch, dextrin, and a hydrolysate of them; disaccharides such as sucrose, maltose, and lactose; and monosaccharides such as glucose and fructose, and these carbohydrates may be used in combination. Examples of vitamins include vitamins A group, B group, C, D, E, and K, folic acid, pantothenic acid, niacin, and biotin, and these vitamins may be used in combination. Examples of minerals other than calcium and magnesium include conventionally used various micronutrients and trace metals such as sodium, potassium, calcium, magnesium, phosphorus, iron, zinc, copper, manganese, iodine, selenium, chromium, and molybdenum that are minerals described in "Dietary Reference Intakes for Japanese (2010)". Additional examples of the minerals include sulfur and cobalt that are regarded as essential minerals, and these minerals may be used in combination. The amount is not particularly limited as long as it is a nutritionally satisfactory amount for a person taking or administering the liquid food composition, but it is preferably that such a compound has characteristics, and used in a state, and an amount that does not impair the liquid nature of the liquid food composition.

As the dietary fiber used in the present invention, usable examples of water-soluble dietary fibers include, in addition to the water-soluble dietary fibers that semi-solidify the liquid food composition in an acidic region, agar, xanthan gum, locust bean gum, gum arabic, collagen, gelatin, fucoidan, glucomannan, polydextrose, starch, and inulin. Examples of insoluble dietary fibers include cellulose, crystalline cellulose, microcrystalline cellulose, hemicellulose, lignin, chitin, chitosan, a corn fiber, and a beet fiber. These dietary fibers may be used in combination.

The liquid food composition of the present invention may use a flavor, a fruit juice, and a functional material. The constitution of nutrient components in the liquid food composition of the present invention is not particularly limited as long as intended nutritional support or nutrition control can be achieved and a person taking or administering the composition can be satisfied, but, for example, for the preparation of a typical enteral nutrition food, blending quantities are controlled so that the protein content will be 0.5 to 10 wt %, the fat content will be 1 to 10 wt %, and the carbohydrate content will be 5 to 40 wt %.

A so-called "liquid diet" may be used as the nutrient component and commercially available products such as Ensure Liquid (registered trademark) from ABBOTT JAPAN Co., Ltd. and MA-7 from Morinaga Milk Industry Co., Ltd. (distributor: Clinico Co., Ltd.) may be used.

In the present invention, the particle size distribution of particles contained in the liquid food composition includes two or more peaks in a neutral region.

Focusing on the particle size distribution of particles contained in the liquid food composition as above, it has been found that, in particular, a composition of which particle size distribution includes two or more peaks is likely to suppress the generation of aggregates.

In the present invention, "particles" mean substances being dispersed and/or suspended in a liquid as a continuous phase in the liquid food composition. The "particles" may be composed of any component as long as they are substances being dispersed and/or suspended in a liquid but the particles are supposed to be composed of independently and/or in combination of the following components; a water-soluble dietary fiber, a metal compound, a protein, an emulsifier, a fat, a nutrient component (such as a carbohydrate and a dietary fiber), and the like.

The particle size distribution of particles in the liquid food composition can be determined and evaluated by using, for example, a particle size distribution analyzer employing laser diffraction/scattering method.

Hereinafter, an example of the determination method of particle size distribution will be described using a laser diffraction/scattering particle size distribution analyzer (LA-950 manufactured by Horiba, Ltd.) as the particle size distribution analyzer.

Analysis conditions of the laser diffraction/scattering particle size distribution analyzer are as follows; dispersion medium: distilled water; sample refractive index: 1.600 to 0.000 i; dispersion medium refractive index: 1.333; circulation rate: 13; and stirring rate: 2. For the analysis, a sample concentration is adjusted so that a light transmission factor (R) is set to 90 to 80% and a transmittance (B) to 90 to 70%. When a liquid food composition is subjected to ultrasonic treatment, the composition is sonicated at an ultrasonic treatment intensity of 3 for 3 minutes, and then the particle size distribution of particles is analyzed in the above analysis conditions for ascertaining the change in the particle size distribution of particles contained in the liquid food composition before and after the ultrasonic treatment.

When the particle size distribution is analyzed in the conditions, the particle size distribution of particles is represented by a distribution curve where the horizontal axis is particle size (nm) and the vertical axis is frequency (%) based on volume in the analysis by the laser diffraction/scattering method. A peak in a particle size distribution in the present invention is a point showing a maximum frequency value in a triangular distribution curve having a base on the horizontal axis (particle size). The starting point and/or the end point of the triangular distribution curve are not necessarily in contact with the horizontal axis (particle size), and a distribution curve of which starting point and/or end point have a frequency (%) of between 0 to 5% can be considered as the triangular distribution.

When a liquid food composition of which pH is in a neutral region has two or more peaks in the particle size distribution of particles which is determined by the method exemplified in the above, such a liquid food composition is regarded as the liquid food composition of the present invention. From the viewpoint of suppressing the generation of aggregates, at least one peak of two or more peaks present in the particle size distribution of particles has a particle size of 3,000 nm or smaller, more preferably a particle size of 2,000 nm or smaller, and even more preferably a particle size of 1,000 nm or smaller.

It is more preferred that ultrasonic treatment of a liquid food composition having a peak of the particle size distribution in such a specific particle size section increases the frequency of the at least one peak having a particle size of 3,000 nm or smaller, more preferably 2,000 nm, and even more preferably a particle size of 1,000 nm or smaller, after the ultrasonic treatment as compared with that before the ultrasonic treatment, and reduces the frequency of at least one peak other than the peak having the increased frequency after the ultrasonic treatment as compared with that before the ultrasonic treatment.

Here, the increase and decrease of a peak frequency before and after the ultrasonic treatment of the liquid food composition can be evaluated by the equation.

(Peak frequency after ultrasonic treatment)/(peak frequency before ultrasonic treatment)×100

Evaluating the peak having the increased frequency after the ultrasonic treatment in accordance with the above equation, the increased peak frequency is 105% or more, preferably 110% or more, even more preferably 120% or more, and furthermore preferably 130% or more with respect to the frequency in the particle size distribution of particles before the ultrasonic treatment. The peak having the reduced frequency after the ultrasonic treatment with the frequency in the particle size distribution of particles before the ultrasonic treatment, has the reduced peak frequency of 60% or less, preferably 50% or less, more preferably 40% or less, and furthermore preferably 30% or less with respect to the frequency in the particle size distribution of particles before the ultrasonic treatment.

When the particle size distribution is determined in the conditions, the particle size distribution of particles is also represented by a distribution curve where the horizontal axis is particle size (nm) and the vertical axis is passing particle integrated value (%) based on volume in the analysis by the laser diffraction/scattering method. An inflection point in the particle size distribution in the present invention is a point where a curvature sign in the distribution curve is changed and a tangential line at the point intersects with the distribution curve itself.

The liquid food composition of the present invention has two or more inflection points and more preferably three or more inflection points in the particle size distribution curve of particles when the particle size distribution of particles in the liquid food composition of which pH is in a neutral region is determined by the method exemplified in the above. From the viewpoint of suppressing the generation of aggregates, it is preferred that at least one point of two or more inflection points present in the particle size distribution curve of particles is present in a particle size section having a particle size of 3,000 nm or smaller, more preferably a particle size of 2,000 nm or smaller, and even more preferably a particle size of 1,500 nm or smaller.

It is preferred that, in the liquid food composition of the present invention, at least one of the inflection points present in the particle size distribution curve of particles is present in a particle section having a particle size of 2,000 nm or smaller, and ultrasonic treatment of the liquid food composition increases a passing particle integrated value (%) corresponding to the at least one inflection point by 5% or more, preferably 10% or more, even more preferably 15% or more, and particularly preferably 20% or more after the ultrasonic treatment as compared with that before the ultrasonic treatment. It is more preferred that the passing particle integrated value (%) corresponding to at least one of the inflection points, the at least one inflection point being present in a particle section having a particle size of 2,000 nm or smaller, is present in a passing particle integrated value section of 25% or more, preferably 35% or more, even more preferably 50% or more, and particularly preferably 75% or more, after the ultrasonic treatment.

The inflection point can be (simply) determined, for example, by the following manner. That is, from passing particle integrated values (%) at an arbitrary particle size (x) nm and a particle size (x+1) nm, the variation in passing particle integrated value (=[integrated value (%) of particle size (x+1)]−[integrated value (%) of particle size (x)]) is calculated. From the variation in passing particle integrated value in each particle size section, the change of curvature of a distribution curve can be ascertained, and a boundary point (a point at which the curvature sign is changed) between a particle size section where the variation in passing particle integrated value increases (the curvature sign is "+") and a particle size section where the variation in passing particle integrated value decreases (the curvature sign is "−") is regarded as the inflection point.

Figure 17:
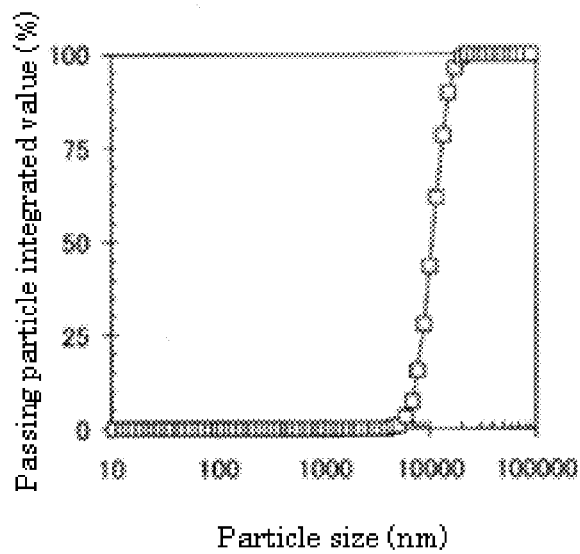
FIG. 17($a$) is a figure showing the particle size distribution of particles in a certain liquid food composition as a distribution curve where vertical axis is passing particle integrated value (%) based on volume and FIG. 17($b$) is a figure showing the relation that is prepared in order to determine an inflection point of the distribution curve shown in FIG. 17($a$), that is between the particle size (nm) and the variation (%) in the passing particle integrated value, and where the horizontal axis is particle size (nm) and the vertical axis is the variation (%) in passing particle integrated value.
Figure 17:
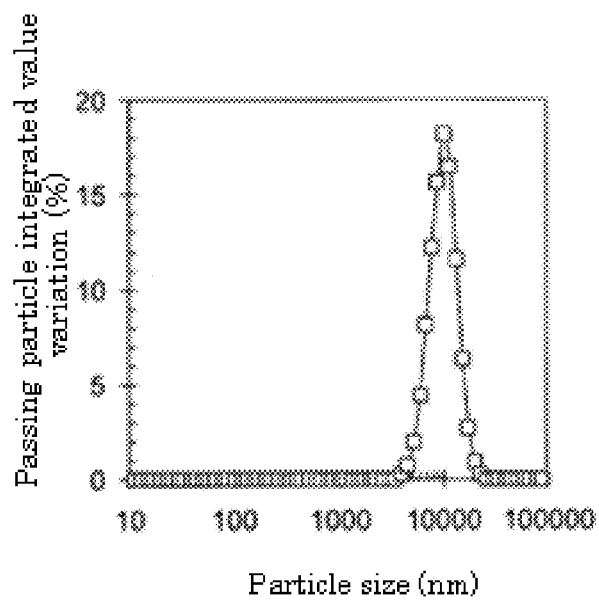

As an example, the particle size distribution of particles in a liquid food composition will be described with reference to FIG. 17(a) and FIG. 17(b). FIG. 17(a) shows the particle size distribution as a distribution curve where the vertical axis is passing particle integrated value (%) based on volume. In FIG. 17(b), the horizontal axis is particle size (nm) and the vertical axis is variation in the passing particle integrated value (%). As shown in FIG. 17(b), in the section having a particle size from about 10 nm and about 3,400 nm or smaller and the section having a particle size of about 30,000 nm or larger, the curvature of the distribution curve has no variation (both variations are 0% in FIG. 17(b)). In the section having a particle size of about 3,400 nm or larger and a particle size of about 10,000 nm or smaller, the curvature of the distribution curve is changed as positive (+) (in FIG. 17(b), the variation increases with the increase of the particle size). In the section having a particle size of about 10,000 nm or larger and about 30,000 nm or smaller, the curvature of the distribution curve is changed as negative (−) (in FIG. 17 (b), the variation decreases with the increase of the particle size). As described above, there is the point where the curvature of the distribution curve is changed at the particle size of around 10,000 nm (in FIG. 17(b), near the peak), and the point is regarded as the inflection point. In other words, in this example, in the distribution curve of the particle size distribution (FIG. 17(a)) where the horizontal axis is particle size (nm) and the vertical axis is passing particle integrated value (%), it is revealed that the inflection point is present at a particle size of around 10,000 nm and a passing particle integrated value of around 47%.

In the present invention, the liquid food composition preferably has an aggregate weight determined by the measurement method below of 0.1 g or less. A liquid food composition having an aggregate weight of more than 0.1 g is likely to cause clogging in a tube at the time of tube feeding or cause granular texture and the like at the time of oral intake. From the viewpoint of the granular texture and swallowing feeling at the time of oral intake, the aggregate weight is more preferably 0.07 g or less, more preferably 0.05 g or less, even more preferably 0.03 g or less, and most preferably 0.01 g or less. A liquid food composition having such an aggregate weight is likely to be judged as less or no granular texture.

Here, the "aggregate" is a substance that is formed during preparation or storage of the liquid food composition and that may cause clogging in a tube at the time of tube feeding or may cause granular texture and the like at the time of oral intake of the liquid food composition. The aggregate is supposed to be composed of particles in the liquid food composition, aggregated particles, a water-soluble dietary fiber, a metal compound, a protein, an emulsifier, a fat, a nutrient component (such as a carbohydrate and a dietary fiber), and the like that are independent of and/or in combination with one another.

The formation amount of the aggregate that may cause the tube clogging or the granular texture can be evaluated by, for example, the weight of a residue after the filtration of the liquid food composition through a nylon screen, a filter paper, or the like.

Hereinafter, a specific example of the measurement method of aggregates in the liquid food composition will be described.

(i) The dry weight (regarded as W1) of a nylon screen (HC-58 (manufactured by NYTAL), mesh: 264 inch) is weighed.

(ii) The nylon screen is placed on a Buchner funnel (pore size: 2 mm) having a diameter of 11 cm, and the Buchner funnel is set to a suction bottle.

(iii) Using ASPIRATOR A-3S (manufactured by EYELA), 200 ml of a liquid food composition is filtered while decompressing the suction bottle.

(iv) The nylon screen after the filtration is dried at 60° C. for 1 hour and cooled to room temperature and then the dry weight (regarded as W2) is weighed.

(v) From the dry weight difference (W2−W1) before and after the filtration, the weight of aggregates obtained as the residue is calculated.

In the present invention, as mentioned above, focusing on the particle size distribution of particles contained in the liquid food composition, it has been found that, in particular, a composition of which particle size distribution includes two or more peaks is likely to suppress the generation of aggregates. It has also been found that a preferred composition has two peaks which undergo certain changes by ultrasonic treatment as above.

While not wishing to be bound by theory, the present inventors suppose the relation between the generation of aggregates and the particle size distribution and/or the change in particle size distribution as follows. It is known that a water-soluble dietary fiber such as alginic acid and pectin generally has poor compatibility with particles (emulsion (an emulsifier or a fat) and with a biopolymer (for example, a protein) in the composition and thus induces the "aggregation" of particles due to various actions such as depletion interaction, electrostatic interaction, and intermolecular cross-linking action. It is believed that particles in a composition are "flocculated" in a step before the step of causing the "aggregation" and then the "flocculated" particles are bonded to generate the "aggregates". In other words, the particles in a "flocculated" state are independent of each other and hence the particles are easily re-dispersed, while the particles in an "aggregated" state are bonded to each other and hence the particles are no longer re-dispersed. In addition, it is supposed that the particles in an "aggregated" state are "flocculated" with each other, and then further aggregated to form larger aggregates.

In the present invention, it is supposed that the composition of which particle size distribution of particles (horizontal axis: particle size (nm), vertical axis: volumetric frequency (%)) has two or more peaks and/or the composition of which particle size distribution of particles is changed by ultrasonic treatment are a result of observing the particles in the "flocculated" state. In other words, it is supposed that the (at least one) peak observed at a particle size of 3,000 nm or smaller in the particle size distribution of particles shows the original particle size of particles, while another peak (observed at a particle size of 1,000 nm or larger) shows the particles in the "flocculated" state. In addition, it is supposed that the increase in the frequency of the (at least one) peak observed at a particle size of 3,000 nm or smaller by ultrasonic treatment of the composition and the reduction in the frequency of the (at least one) peak other than the peak having the increased frequency shows the phenomenon of re-dispersion of the particles in the flocculated state, which can be explained by the suggestion above. In contrast, a single peak observed in the particle size distribution of a conventional liquid food composition is supposed to be a result of observing the particles in the "aggregated" state above, and it is supposed that such particles are no-longer re-dispersed to readily generate aggregates. As described above, by the evaluation of particles present in the composition while distinguishing between the "flocculation" and the "aggregation", the generation of aggregates during preparation and/or during storage of the composition can be appropriately evaluated for the first time. Such an evaluation can lead to the suppression of the aggregate generation during preparation and/or during storage of the composition. Consequently, the liquid food composition that is unlikely to cause clogging in a tube and has good tube passage performance at the time of tube feeding, has less "granular texture" and good "swallowing feeling" at the time of oral intake, and is consequently easy to be taken can be provided.

The method for producing the liquid food composition of the present invention is not particularly limited but the liquid food composition can be prepared in usual ways. For example, to water, a water-soluble dietary fiber (a), a metal compound (b) containing a necessary mineral component for humans and not causing gelation of the water-soluble dietary fiber (a) in a neutral region, a protein (c), an emulsifier (d), as well as a fat (e), and other nutrient components (f) such as a protein, a carbohydrate, vitamins and minerals are appropriately added; the whole is mixed; and the mixture is homogenized with a high-pressure emulsification equipment, a homogenizer, or the like. The prepared liquid food composition may be filled in a pouch such as a soft bag and an aluminum pouch and a container such as a paper package, a can, and a bottle; and subjected to common sterilization treatment such as heat and pressure sterilization using a retort, an autoclave, or the like, energized thermal sterilization, and microwave heat sterilization. Such a sterilization treatment can suppress the alteration of physical properties of the liquid food composition due to microorganisms and the like. The sterilization treatment may also be carried out after the filling of the liquid food composition in a container, but any method may be employed as long as the alteration of physical properties of the liquid food composition due to microorganisms and the like can be suppressed.

The container filled with the liquid food composition may be composed of any material and may have any form, but the container used in the present invention preferably has a form by which physical properties of the liquid food composition are not altered due to the contamination of microorganisms and the like. Furthermore, from the viewpoint of suppressing the reduction of nutrient components such as vitamins, the container is preferably made from a material having light blocking properties and/or gas barrier properties, but the container may be transparent. The liquid food composition of the present invention does not impair the liquid nature of the composition even when a water-soluble dietary fiber is preliminarily added and hence the water-soluble dietary fiber (a) and other all components such as a metal compound (b), a protein (c), and an emulsifier (d) can be filled in a container. In the present invention, the state filling a liquid food composition in a container as above is referred to as a "one-pack type product". In contrast, as related arts disclosed in Patent Documents 1 and 2, a product including a liquid food and a gelling agent such as a water-soluble dietary fiber that are separately packed is referred to as a "two-pack type product". In addition, a product including a liquid food and a gelling agent such as a water-soluble dietary fiber in a container of which inside is separated by a partition wall or the like so that the liquid food and the gelling agent are not mixed is also referred to as a "two-pack type product".

The liquid food composition of the present invention prepared as above is a one-pack type product to which a water-soluble dietary fiber is preliminarily added, but undergoes little change in physical properties such as solidification and separation of components during production process and distribution as well as even during storage, and consequently can stably sustain the quality for a long time. As a result, a liquid food composition having an advantage that the composition is liquid before entering the stomach and is thickened and/or semi-solidified in the stomach can be practically supplied to the market. In addition, the liquid food composition that is unlikely to cause clogging in a tube and has good tube passage performance at the time of tube feeding, has less "granular texture" and good "swallowing feeling" at the time of oral intake, and is consequently easy to be taken can be provided because the generation of aggregates can be suppressed during preparation and/or during storage of the composition.

The liquid food composition of the present invention can employ a commonly used distribution condition and storage condition and can be distributed and stored in a temperature condition of 0° C. to 40° C. However, the distribution and storage are preferably at 4° C. to 30° C. and more preferably at 4° C. to 25° C. Distribution and/or storage in a condition of less than 0° C. may lead to the freeze of water in the liquid food composition to separate food components, while distribution and/or storage in a condition of more than 40° C. may lead to the reduction of nutrient components such as vitamins in the liquid food composition. The liquid food composition of the present invention can be distributed and stored either in a bright place or in a dark place, but from the viewpoint of suppressing the reduction of nutrient components such as vitamins, the liquid food composition is preferably distributed and stored in a dark place.

The liquid food composition of the present invention can be taken by a conventional method such as oral intake and tube feeding. For example, the liquid food composition can be taken directly from a mouth and can be taken dropwise through a tube from a container hung on a stand. The liquid food composition can be forcibly taken, for example, using a pump or a pressure bag or by pressurizing a container by hand, but the intake method is not limited to them. The viscosity of the liquid food composition is not particularly limited as long as the easiness in intake is not impaired by each intake method, but the viscosity is less than 1,000 cP, preferably 500 cP or less, more preferably 400 cP or less, even more preferably 300 cP or less, and furthermore preferably 200 cP or less. A liquid food composition having a viscosity of 1,000 cP or more may be difficult to pass through a tube or the like to impair the easiness in intake. When the liquid food composition is orally taken, from the viewpoint of granular texture and swallowing feeling, a composition having a viscosity of 170 cP or less gives thickness feeling but easily taken. For swallowing feeling and easy intake, the composition has a viscosity of 150 cP or less, preferably 135 cP or less, more preferably 100 cP or less, even more preferably 85 cP or less, and most preferably 80 cP or less.

The liquid food composition of the present invention is semi-solidified in an acidic region in the stomach. Accordingly, the liquid food composition is expected to have, for example, the prevention effect of gastroesophageal reflux disease, aspiration pneumonia, diarrheal disease, leakage from a fistula, and the like and the effects on relief of the feeling of hunger and on suppression of sudden increase in blood glucose level. The pH at the time of the semi-solidification is not particularly limited, but from the viewpoint of good semi-solidification in an acidic environment in the stomach, a composition that is semi-solidified at a pH of 5.5 or less is preferred, that is semi-solidified at a pH of 5.0 or less is more preferred, that is semi-solidified at a pH of 4.8 or less is even more preferred, and that is semi-solidified at a pH of 4.5 or less is particularly preferred.

Using the above advantages, the liquid food composition of the present invention can be used for a nutrition food, an enteral nutrition food, an enteral nutrient including a diet classified as a medicinal supplies, an elemental diet, a polymeric formula, an oligomeric formula, a high density liquid diet, a diet food, a food for diabetes, and the like. As described above, the liquid food composition of the present invention can be taken by a method such as oral intake and tube feeding. The intake method is not particularly limited but the liquid food composition is suitable as an enteral nutrition food or an enteral nutritional supplement that is taken through a tube such as a nasogastric tube or a tube from a gastrostomy.

EXAMPLES

Hereinafter, examples and comparative examples will be described in order to specifically explain the present invention, but the present invention is not limited to them.

For the evaluation of physical properties representing the feature of the present invention, the following examinations were carried out.

<Determination of Viscosity of Liquid Food Composition>

The viscosity of a liquid food composition was determined with a "Brookfield viscometer (manufactured by Tokimec, Inc.)". Specifically, a sample for measurement was charged into a glass container having an inner diameter of 60 mm, then the viscosity was measured three times in a condition at a liquid temperature of 25° C. using a No. 2 rotor at a rotation speed of 60 revolutions per minute and a holding time of 30 seconds, and the mean value was calculated as a measured value (viscosity).

<Ascertainment of Semi-Solidification of Liquid Food Composition in Acidic Region and Calculation of Solidification Ratio>

The ascertainment of semi-solidification of a liquid food composition in an acidic region was carried out in the following manner. A solidification ratio was calculated in Examples 3 and 4, Comparative Examples 3 to 5, and the dependency evaluation on the amount of an emulsifier added described later.

(1) Into a 50-ml plastic tube, 20 g of artificial gastric juice (the Japanese Pharmacopoeia) kept at 37° C. is charged.

(2) Into the artificial gastric juice, 10 g of a liquid food composition stored at 25° C. is charged, the plastic tube containing the artificial gastric juice and the liquid food composition is weighed (regarded as [tube weight before filtration]).

(3) The plastic tube is gently stirred with a "HL-2000 HybriLinker (manufactured by UVP Laboratory Products)". Specifically, the tube is fixed to a fixture in a chamber, a motor control knob of the apparatus is set at "MIN", and the tube is stirred in a condition at 37° C. for 2 minutes 30 seconds.

(4) A solid is collected on a nylon screen (40 mesh; manufactured by Sogo Laboratory Glass Works Co., Ltd.) by filtration under vacuum to remove a liquid portion; then the solid with the nylon screen is placed on a paper towel or the like and excess water is removed for 2 minutes; the solid with the nylon screen is weighed (regarded as [solid weight after filtration]); and the plastic tube after washing the content liquid is weighed ([tare weight after filtration]).

(5) The solid residue on the nylon screen is ascertained. The solidification ratio is calculated in accordance with Equation (1).

[Mathematical Formula 1]

$$\text{Solidification ratio (\%)} = \frac{[\text{Solid weight after filtration}] - [\text{Nylon screen weight}]}{[\text{Tube weight before filtration}] - [\text{Tare weight after filtration}] - [\text{Artificial gastric juice weight}]} \times 100 \quad \text{Equation (1)}$$

<Determination of Particle Size Distribution of Liquid Food Composition>

In Examples 1, 3, and 4, Comparative Examples 3 to 5, and the dependency evaluation on the amount of an emulsifier added, in accordance with the method described above using a laser diffraction/scattering particle size distribution analyzer (LA-950 manufactured by Horiba, Ltd.) as a particle size distribution analyzer, the particle size distribution of aggregates in a liquid food composition was determined.

<Weighing of Aggregate in Liquid Food Composition>

In accordance with the above weighing method of aggregates in a liquid food composition using a nylon screen, the weight of aggregates was calculated from the dry weight difference before and after filtration.

<Evaluation by Oral Intake>

In Examples 1, 3, and 4, Comparative Examples 3 to 5, and the dependency evaluation on the amount of an emulsifier added described later, the liquid food composition was evaluated in oral intake. The evaluation was carried out by the presence or absence of granular texture and swallowing feeling as indices. For the granular texture evaluation, a composition having the granular texture at the time of oral intake is evaluated as "presence", while a composition without the granular texture is evaluated as "absence". For the swallowing feeling evaluation, a composition capable of being taken with good swallowing feeling is evaluated as "A", a composition that has thickness feeling but is readily taken is evaluated as "B", and a composition that has poor flowability and is difficult to be taken is evaluated as "C".

Reference Example 1

To 400 ml distilled water, 2.5 g of sodium alginate (KIMICAALGIN IL-2: manufactured by KIMICA corporation) was added to prepare 0.5 wt % aqueous sodium alginate solution. Next, 1.15 g of calcium carbonate and 0.75 g of magnesium carbonate were mixed to the aqueous sodium alginate solution. The mixture was cooled to room temperature, and then added with distilled water to make the volume 500 ml. A soft bag (R1420H: manufactured by Meiwa Pax Co., Ltd.) was filled with 200 g of the prepared liquid food composition, and the whole was sterilized (121° C., 20 minutes) in an autoclave sterilizer.

The prepared product was liquid and had a pH of 9.9 and a viscosity of 10 cP. Ascertaining the semi-solidification in an acidic condition, the prepared product was semi-solidified in an artificial gastric juice and gave a solid residue on a nylon screen. Even after standing storage (25° C.) for a month, the prepared product was not changed in the pH and viscosity and also in the degree of semi-solidification in the acidic condition.

In this manner, it was ascertained that the liquid food composition containing sodium alginate, the calcium compound having poor solubility in a neutral region, and the magnesium compound having poor solubility in a neutral region as basic components did not undergo the change in the liquid nature during preparation and even after storage and was semi-solidified in an acidic condition. In addition, the prepared product was a liquid food composition capable of satisfying nutritional requirements because the magnesium compound was added.

Example 1

Based on the formulation described in Table 1, a liquid food composition containing 0.5 wt % sodium alginate was prepared.

TABLE 1

| Component | Example 1 | Comparative Example 1 | Comparative Example 2 |
|---|---|---|---|
| Sodium alginate | 0.5 g | 0.5 g | 0.5 g |
| Dextrin | 12.2 g | 12.2 g | 12.2 g |
| Soybean protein | 4.3 g | 4.3 g | — |
| Sodium caseinate | — | — | 4.3 g |
| Fat (including emulsifier) | 3.4 g | 3.4 g | 3.4 g |
| Calcium carbonate | 230 mg | — | 230 mg |
| Calcium dihydrogen phosphate | — | 580 mg | — |
| Magnesium carbonate | 150 mg | — | 150 mg |
| Magnesium sulfate | — | 420 mg | — |
| Other minerals | 1330 mg | 1330 mg | 1330 mg |
| Vitamins | 62 mg | 62 mg | 62 mg |
| Distilled water | Balance | Balance | Balance |
| Total | 100 ml | 100 ml | 100 ml |
| pH | 6.7 | — | 6.8 |
| Viscosity | 110 | — | 110 |
| Generation frequency of solid | None | Gelated | None |
| Occurrence degree of component separation *) | A | /**) | B |

*) A: Component separation was not occurred
B: Component separation was occurred
**) Evaluation was impossible due to gelation To 650 ml of distilled water, 5 g of sodium alginate was added. Next, a dextrin powder and a soybean protein powder (manufactured by Fuji Oil Co., Ltd.) were added. A fat (containing an emulsifier) was further added, then calcium carbonate, magnesium carbonate, other minerals, and vitamins were sequentially added, and the whole was stirred. The other minerals used were a mixture of a zinc-containing yeast, a copper-containing yeast, a manganese-containing yeast, a chromium-containing yeast, a selenium-containing yeast, a molybdenum-containing yeast (these mineral-containing yeasts: manufactured by Medience Corporation), and ferric sodium citrate (manufactured by Ebisu Co., Ltd.). Then, distilled water was added to make the volume 1,000 ml and the mixture was homogenized with a Manton Gaulin high-pressure emulsification equipment (Rannie 2000: manufactured by APV) (for the first time: 20 MPa, for the second time: 48 MPa). Each soft bag (R1420H: manufactured by Meiwa Pax Co., Ltd.) was filled with 200 g of the prepared liquid food composition containing 0.5 wt % sodium alginate, and the whole was sterilized (121° C., 20 minutes) in an autoclave sterilizer.

The liquid food composition was a uniform liquid and the generation of solids and the separation of nutrient components were not observed. The liquid food composition had a pH of 6.7 and a viscosity of 110 cP and showed flowability. Ascertaining the semi-solidification in an acidic condition, the liquid food composition was semi-solidified in an artificial gastric juice and gave a solid residue on a nylon screen. The pH, the viscosity, the generation degree of solids, and the occurrence degree of component separation of the liquid food composition are shown in Table 1.

Even after standing storage (25° C.) for three months, the liquid food composition was not changed in the pH and viscosity and was little changed during storage in physical properties, for example, component separation. The degree of semi-solidification in the acidic condition was also not changed.

In this manner, it was ascertained that the liquid food composition containing sodium alginate, the calcium compound having poor solubility in a neutral region, the magnesium compound having poor solubility in a neutral region, the metal compounds of zinc, copper, manganese, chromium, selenium, and molybdenum included in yeasts, the iron compound in a small amount not causing gelation of sodium alginate, and the soybean protein as basic components sustained the liquid nature during preparation and even after storage, underwent little change in physical properties, for example, little component separation, and was semi-solidified in an acidic condition. In addition, it was a liquid food composition capable of satisfying nutritional requirements because the mineral components necessary for humans and the protein were added.

Analyzing the particle size distribution of particles in the liquid food composition (Example 1), as shown in FIG. 1(a), the particle size distribution had two peaks and the smaller peak was present in a section having a particle size of 3,000 nm or smaller (at a particle size of 259 nm and a frequency of 6.940%). The ultrasonic treatment reduced the frequency of the larger peak and increased the frequency of the smaller peak present in the section having a particle size of 3,000 nm or smaller. Evaluating each peak frequency increased or reduced before and after the ultrasonic treatment by the aforementioned equation (peak frequency after ultrasonic treatment)/(peak frequency before ultrasonic treatment)×100), the smaller peak having the increased peak frequency was 154% (=10.700%/6.940%×100), while the larger peak having the reduced peak frequency was 47% (=2.548%15.401%×100).

As shown in FIG. 1(b), representing the particle size distribution of the liquid food composition (Example 1) as a distribution curve where the vertical axis is passing particle integrated value (%) based on volume, the particle size distribution curve had three inflection points of (1) at a passing particle integrated value of around 20.23% and a particle size of around 226 nm, of (2) at around 39.75% and around 669 nm, and of (3) at around 74.55% and around 5,133 nm. The passing particle integrated value of the inflection point (2) increased by 21% after the ultrasonic treatment as compared with that before the ultrasonic treatment, and the inflection point (2') after the ultrasonic treatment was at around 60.86% and around 669 nm.

The liquid food composition had less granular texture and good swallowing feeling at the time of oral intake and was readily taken.

Comparative Example 1

Based on the formulation described in Table 1, a liquid food composition containing 0.5 wt % sodium alginate was prepared in a similar manner to that in Example 1.

The calcium compound used was "calcium dihydrogen phosphate monohydrate" and the magnesium compound used was "magnesium sulfate heptahydrate". These compounds are metal salts soluble in a neutral region.

In the liquid food composition, the generation of solids was observed during the production process and the whole turned into a gel after the sterilization treatment.

This is supposed to be because although the Ca amount and the Mg amount were the same but the soluble calcium compound and the soluble magnesium compound were used and divalent ions of calcium ions and magnesium ions derived from the compounds caused the gelation of sodium alginate.

In this manner, when the soluble calcium compound and the soluble magnesium compound were used, the intended liquid food composition of the present invention could not be prepared.

Comparative Example 2

Based on the formulation described in Table 1, a liquid food composition containing 0.5 wt % sodium alginate was prepared in a similar manner to that in Example 1.

The protein source used was sodium caseinate in place of the soybean protein.

The obtained food composition was liquid and had a pH of 6.8 and a viscosity before semi-solidification of 110 cP. Ascertaining the semi-solidification in an acidic condition, the liquid food composition was semi-solidified in an artificial gastric juice to give a solid residue on a nylon screen. However, after the sterilization treatment of the liquid food composition, the components were separated into two layers. The pH, the viscosity, the generation degree of solids, and the occurrence degree of component separation of the liquid food composition are shown in Table 1.

In this manner, when sodium caseinate as a milk protein was used in place of the soybean protein as a plant protein, the food composition did not entirely turn into a gel but caused component separation and the intended liquid food composition of the present invention could not be prepared.

Example 2

In a similar manner to that in Example 1, liquid food compositions (1) without sodium alginate, (2) containing 0.3 wt % sodium alginate, (3) containing 0.5 wt % sodium alginate, (4) containing 1.0 wt % sodium alginate, and (5) containing 1.5 wt % sodium alginate were prepared. The sodium alginates used were "KIMICAALGIN IL-2: manufactured by KIMICA corporation" in (2) to (4) and "KIMICAALGIN IL-1: manufactured by KIMICA corporation" in (5), while the protein source used was a soybean protein.

TABLE 2

| | (1) | (2) | (3) | (4) | (5) |
|---|---|---|---|---|---|
| | | Concentration of sodium alginate | | | |
| | Without addition | 0.3 wt % IL2 | 0.5 wt % IL2 | 1.0 wt % IL2 | 1.5 wt % IL1 |
| pH | 6.8 | 6.8 | 6.7 | 7.3 | 7.3 |
| Viscosity | 35 | 80 | 110 | 195 | 190 |

TABLE 2-continued

|  | (1) | (2) | (3) | (4) | (5) |
|---|---|---|---|---|---|
|  |  | Concentration of sodium alginate | | | |
|  | Without addition | 0.3 wt % IL2 | 0.5 wt % IL2 | 1.0 wt % IL2 | 1.5 wt % IL1 |
| Degree of semi-solidification*) | C | B | A | A | A |

*)C: Not semi-solidified
B: A semi-solidified product was observed on a nylon screen.
A: Most was semi-solidified to give a residue on a nylon screen.

Each food composition obtained was liquid.

Ascertaining the semi-solidification in an acidic condition, (1) the composition without sodium alginate was completely mixed with the artificial gastric juice and no solid was observed on a nylon screen. Each of the liquid food compositions (2) to (5) was semi-solidified in the artificial gastric juice and gave a solid residue on a nylon screen. The pH, the viscosity before semi-solidification, and the degree of semi-solidification of each liquid composition are shown in Table 2.

Example 3

Based on the formulation described in Table 3, a liquid food composition containing lysolecithin as an emulsifier was prepared in the following manner.

To 223 ml of distilled water, 3.6 g of lysolecithin (manufactured by Tsuji Oil Mills Co., Ltd., product name: SLP-WhiteLyso, HLB value: about 12) and 36 g of a fat (corn oil) were added, and while stirring, the whole was homogenized (20 MPa) with a Manton Gaulin high-pressure emulsification equipment (Rannie 2000: manufactured by APV) to give 260 ml of an emulsion.

Next, to 320 ml of distilled water, 173 ml of the emulsion was added. While stirring at an adequate speed, the distilled water and the emulsion were mixed, and then 7 g of sodium alginate was added. Next, a dextrin powder and a soybean protein (manufactured by Fuji Oil Co., Ltd.) were added until completely dissolved. Then, a phosphate, calcium carbonate, magnesium carbonate, other minerals, and vitamins were sequentially added, and the whole was stirred. Then, distilled water was added to make the volume 700 ml and the mixture was homogenized with a Manton Gaulin high-pressure emulsification equipment (for the first time: 20 MPa, for the second time: 48 MPa). Each soft bag (R1420H: manufactured by Meiwa Pax Co., Ltd.) was filled with 200 g of the prepared liquid food composition, and the whole was sterilized (121° C., 20 minutes) in an autoclave sterilizer.

Figure 2:
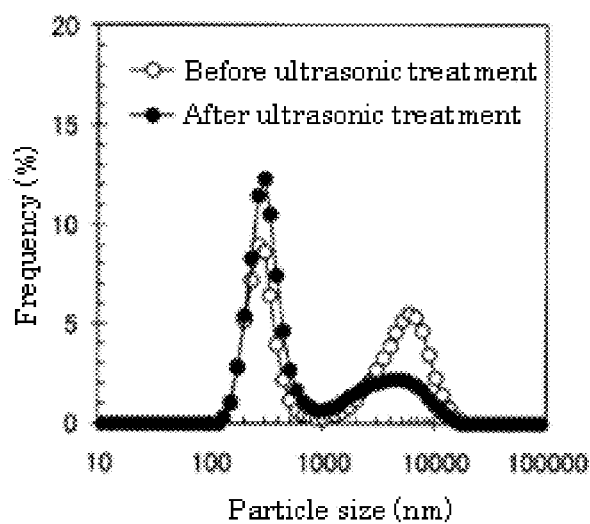
FIG. 2($a$) is a figure showing the particle size distribution of particles in a liquid food composition of Example 3 and FIG. 2($b$) is a figure showing the particle size distribution of particles in the liquid food composition of Example 3 as a distribution curve where vertical axis is passing particle integrated value (%) based on volume.
Figure 2:
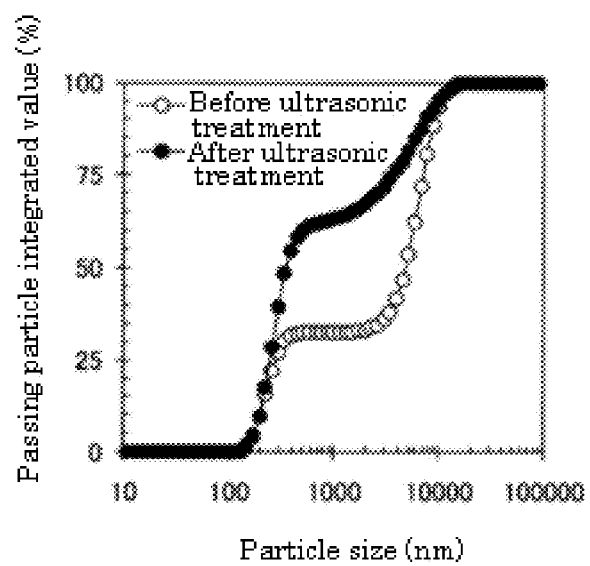

The liquid food composition was a uniform liquid and the generation of solids and the separation of nutrient components were not observed. The liquid food composition had a solidification ratio of 51%, an aggregate weight of 0.01 g, and a viscosity before semi-solidification of 77 cP. As shown in FIG. 2(a), the particle size distribution of the liquid food composition had two peaks and the smaller peak was present in a section having a particle size of 3,000 nm or smaller (a particle size of 259 nm). The ultrasonic treatment reduced the frequency of the larger peak and increased the frequency of the smaller peak present in the section having a particle size of 3,000 nm or smaller. Evaluating each peak frequency increased or reduced before and after the ultrasonic treatment by the aforementioned equation ((peak frequency after ultrasonic treatment)/(peak frequency before ultrasonic treatment)×100), the smaller peak having the increased peak frequency was 137% (=12.32%/8.999%×100), while the larger peak having the reduced peak frequency was 40% (=2.188%/5.482%×100).

As shown in FIG. 2(b), representing the particle size distribution of the liquid food composition as a distribution curve where the vertical axis is passing particle integrated value (%) based on volume, the particle size distribution curve had three inflection points of (1) at a passing particle integrated value of around 15.79% and a particle size of around 226 nm, of (2) at around 33.76% and around 877 nm, and of (3) at around 62.21% and around 5,876 nm. The passing particle integrated value of the inflection point (2) increased by 29% after the ultrasonic treatment as compared with that before the ultrasonic treatment, and the inflection point (2') after the ultrasonic treatment was at around 62.92% and around 877 nm.

The liquid food composition had less granular texture and good swallowing feeling at the time of oral intake and was readily taken.

Example 4

Based on the formulation described in Table 3, a liquid food composition was prepared in a similar manner to that in Example 3 except that sucrose laurate (manufactured by Mitsubishi-Kagaku Foods Corporation (product name: Ryoto Sugar Ester L-1695, HLB value: 16)) was used in place of lysolecithin as the emulsifier.

Figure 3:
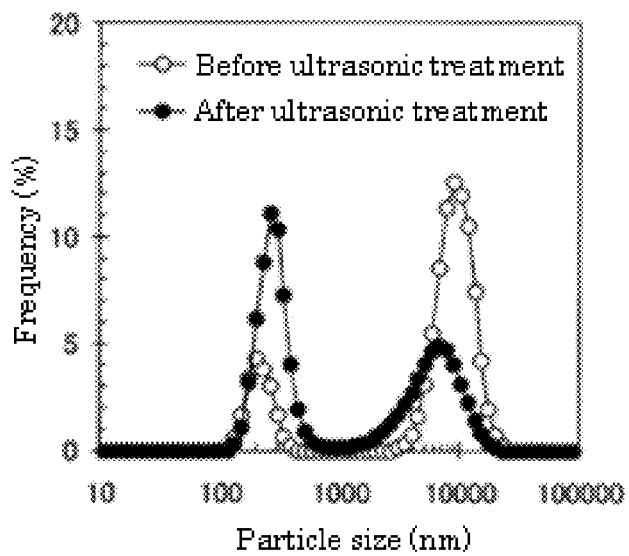
FIG. 3($a$) is a figure showing the particle size distribution of particles in a liquid food composition of Example 4 and FIG. 3($b$) is a figure showing the particle size distribution of particles in the liquid food composition of Example 4 as a distribution curve where vertical axis is passing particle integrated value (%) based on volume.
Figure 3:
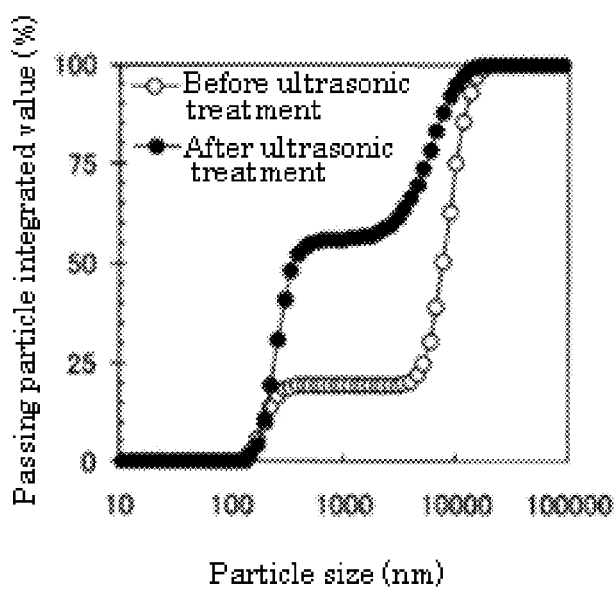

The liquid food composition was a uniform liquid and the generation of solids and the separation of nutrient components were not observed. The liquid food composition had a solidification ratio of 46%, an aggregate weight of 0.07 g, and a viscosity before semi-solidification of 161 cP. As shown in FIG. 3(a), the particle size distribution of the liquid food composition had two peaks and the smaller peak was present in a section having a particle size of 3,000 nm or smaller (a particle size of 197 nm). The ultrasonic treatment reduced the frequency of the larger peak and increased the frequency of the smaller peak present in the section having a particle size of 3,000 nm or smaller. Evaluating each peak frequency increased or reduced before and after the ultrasonic treatment by the aforementioned equation, the smaller peak having the increased peak frequency was (11.13/4.269×100) 261%, while the larger peak having the reduced peak frequency was 38% (=4.882%/12.528%×100).

As shown in FIG. 3(b), representing the particle size distribution of the liquid food composition as a distribution curve where the vertical axis is passing particle integrated value (%) based on volume, the particle size distribution curve had three inflection points of (1) at a passing particle integrated value of around 5.70% and a particle size of around 172 nm, of (2) at around 19.30% and around 1,005 nm, and of (3) at around 50.44% and around 7,696 nm. The passing particle integrated value of the inflection point (2) increased by 37% after the ultrasonic treatment as compared with that before the ultrasonic treatment, and the inflection point (2') after the ultrasonic treatment was at around 56.11% and around 1,005 nm.

The liquid food composition had less granular texture and a little thickness feeling at the time of oral intake but was readily taken.

Comparative Example 3

Based on the formulation described in Table 3, a liquid food composition was prepared in a similar manner to that in Example 3 except that lecithin (manufactured by Wako, HLB value: about 3.5) was used in place of lysolecithin as the emulsifier.

The liquid food composition had a solidification ratio of 36%, an aggregate weight of 0.3 g, and a viscosity before semi-solidification of 190 cP. Comparing with the liquid food composition of Example 3, it had a lower solidification ratio and was liquid but in a non-uniform state, for example, the aggregates were visually observed, and also it had a high viscosity.

Figure 4:
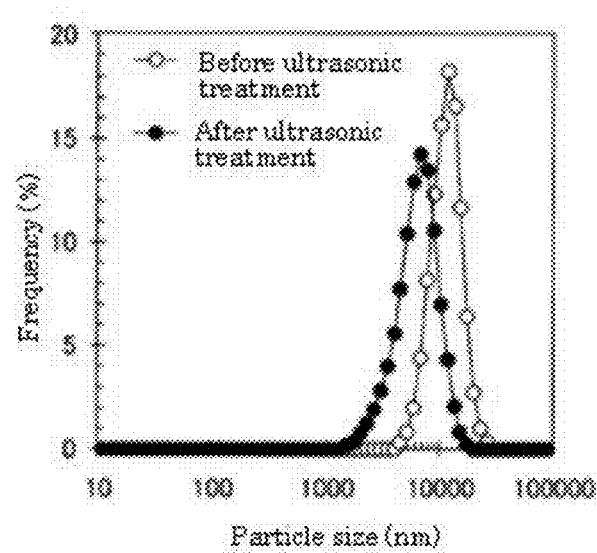
FIG. 4($a$) is a figure showing the particle size distribution of particles in a liquid food composition of Comparative Example 3 and FIG. 4($b$) is a figure showing the particle size distribution of particles in the liquid food composition of Comparative Example 3 as a distribution curve where vertical axis is passing particle integrated value (%) based on volume.
Figure 4:
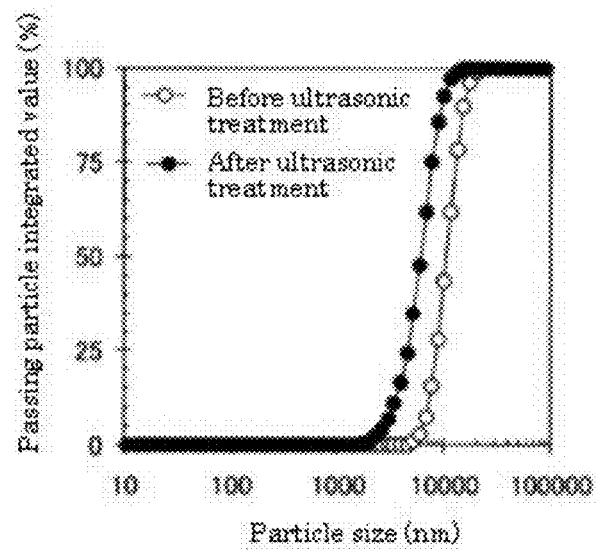

As shown in FIG. 4(a), the particle size distribution of the liquid food composition had a peak in a section having a particle size of 3,000 nm or larger. The ultrasonic treatment reduced the frequency of the peak but no peak was observed in a section having a particle size of 3,000 nm or smaller.

As shown in FIG. 4(b), representing the particle size distribution of the liquid food composition as a distribution curve where the vertical axis is passing particle integrated value (%) based on volume, the particle size distribution curve had an inflection point at a passing particle integrated value of around 42.43% and a particle size of around 10,097 nm. The passing particle integrated value increased by 5% after the ultrasonic treatment as compared with that before the ultrasonic treatment, and the inflection point after the ultrasonic treatment was at around 47.54% and around 5,867 nm.

The liquid food composition had granular texture and poor flowability at the time of oral intake and was difficult to be taken.

Figure 13:
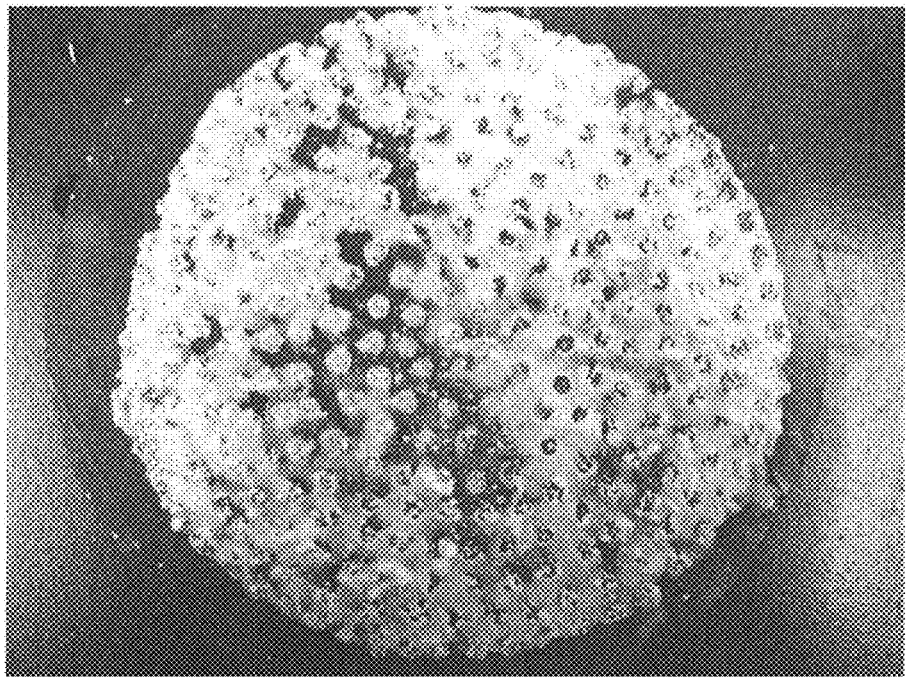
FIG. 13 is a figure showing the generation state of aggregates as a residue after the liquid food composition of Comparative Example 3 was filtered.

In a similar manner to the weighing of the aggregates, the liquid composition was filtered and the generation of aggregates as the residue was shown in FIG. 13. In the figure, the white parts are aggregates and the figure reveals the generation of a large amount of aggregates.

Comparative Example 4

Based on the formulation described in Table 3, a liquid food composition was prepared in a similar manner to that in Example 3 except that diacetyl tartrate (manufactured by Taiyo Kagaku Co., Ltd. (product name: Sunsoft No. 641D, HLB value: 9.0)) was used in place of lysolecithin as the emulsifier.

Figure 5:
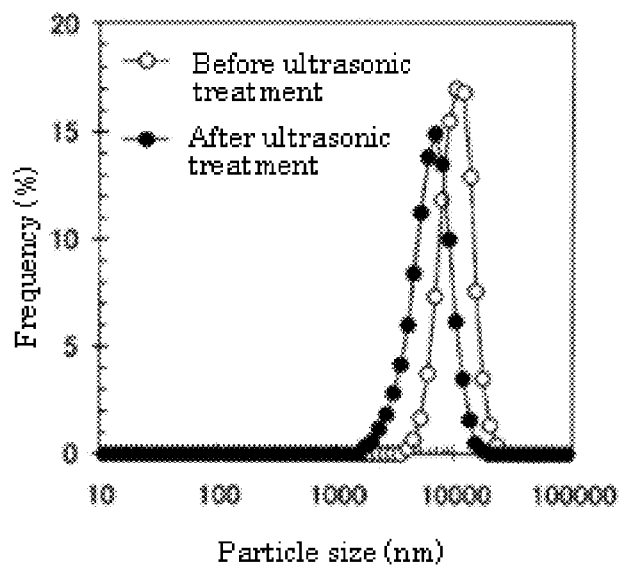
FIG. 5($a$) is a figure showing the particle size distribution of particles in a liquid food composition of Comparative Example 4 and FIG. 5($b$) is a figure showing the particle size distribution of particles in the liquid food composition of Comparative Example 4 as a distribution curve where vertical axis is passing particle integrated value (%) based on volume.
Figure 5:
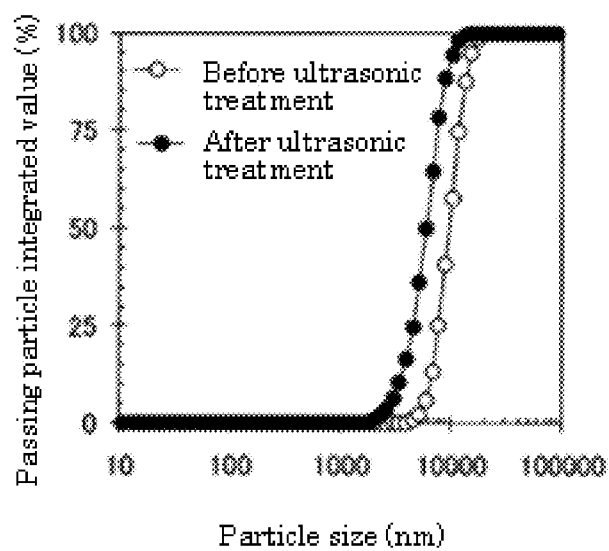

The liquid food composition had a solidification ratio of 41%, an aggregate weight of 0.14 g, and a viscosity before semi-solidification of 182 cP. Comparing with the liquid food composition of Example 3, it had a lower solidification ratio and was liquid but in a non-uniform state, for example, the aggregates were visually observed, and also it had a high viscosity. As shown in FIG. 5(a), the particle size distribution of the liquid food composition had a peak in a section having a particle size of 1,000 nm or larger. The ultrasonic treatment reduced the frequency of the peak but no peak was observed in a section having a particle size of 1,000 nm or smaller.

As shown in FIG. 5(b), representing the particle size distribution of the liquid food composition as a distribution curve where the vertical axis is passing particle integrated value (%) based on volume, the particle size distribution curve had an inflection point at a passing particle integrated value of around 40.75% and a particle size of around 8,816 nm. The passing particle integrated value increased by 9% after the ultrasonic treatment as compared with that before the ultrasonic treatment, and the inflection point after the ultrasonic treatment was at around 49.93% and around 5,867 nm.

The liquid food composition had granular texture and poor flowability at the time of oral intake and was difficult to be taken.

Figure 14:
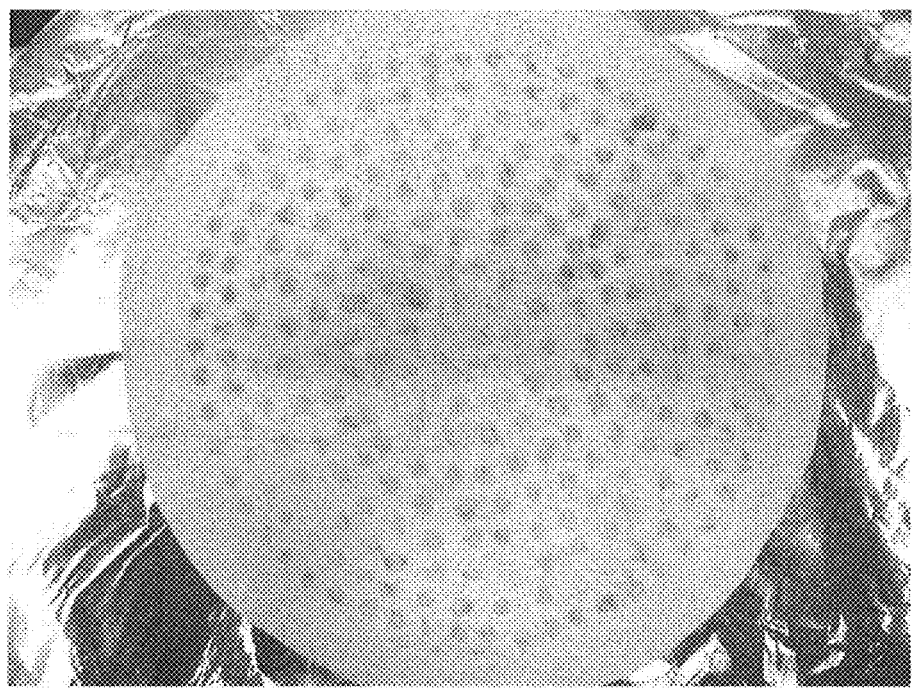
FIG. 14 is a figure showing the generation state of aggregates as a residue after the liquid food composition of Comparative Example 4 was filtered.

In a similar manner to the weighing of the aggregates, the liquid composition was filtered and the generation of aggregates as the residue was shown in FIG. 14. In the figure, dotted dark parts having an approximately circular shape are aggregates, the aggregates are observed all over the nylon screen, and the figure reveals the generation of a large amount of aggregates.

Comparative Example 5

Based on the formulation described in Table 3, a liquid food composition was prepared in a similar manner to that in Example 3 except that hexaglycerol tristearate (manufactured by Sakamoto Yakuhin Kogyo Co., Ltd. (product name: TS-5S, HLB value: 7.0)) was used in place of lysolecithin as the emulsifier.

Figure 6:
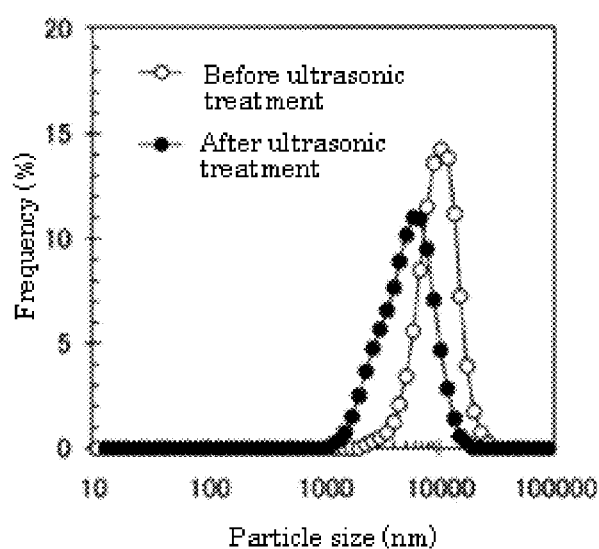
FIG. 6($a$) is a figure showing the particle size distribution of particles in a liquid food composition of Comparative Example 5 and FIG. 6($b$) is a figure showing the particle size distribution of particles in the liquid food composition of Comparative Example 5 as a distribution curve where vertical axis is passing particle integrated value (%) based on volume.
Figure 6:
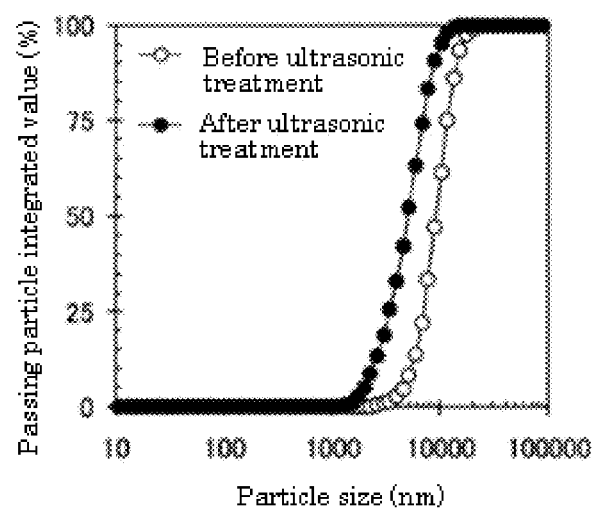

The liquid food composition had a solidification ratio of 44%, an aggregate weight of 0.13 g, and a viscosity before semi-solidification of 185 cP. Comparing with the liquid food composition of Example 3, it had a lower solidification ratio and was liquid but in a non-uniform state, for example, the aggregates were visually observed, and also it had a high viscosity. As shown in FIG. 6(a), the particle size distribution of the liquid food composition had a peak in a section having a particle size of 3,000 nm or larger. The ultrasonic treatment reduced the frequency of the peak but no peak was observed in a section having a particle size of 3,000 nm or smaller.

As shown in FIG. 6(b), representing the particle size distribution of the liquid food composition as a distribution curve where the vertical axis is passing particle integrated value (%) based on volume, the particle size distribution curve had an inflection point at a passing particle integrated value of around 47.17% and a particle size of around 8,816 nm. The passing particle integrated value increased by 5% after the ultrasonic treatment as compared with that before the ultrasonic treatment, and the inflection point after the ultrasonic treatment was at around 52.20% and around 5,122 nm.

The liquid food composition had granular texture and poor flowability at the time of oral intake and was difficult to be taken.

The evaluation results of Examples 3 and 4 and Comparative Examples 3 to 5 are listed in Table 4.

TABLE 3

| | | Example | | Comparative Example | | |
| --- | --- | --- | --- | --- | --- | --- |
| Component composition (unit: g) | | 3 | 4 | 3 | 4 | 5 |
| Water-soluble dietary fiber | Sodium alginate | 1.0 | 1.0 | 1.0 | 1.0 | 1.0 |
| Minerals | Calcium carbonate | 0.190 | 0.190 | 0.190 | 0.190 | 0.190 |
| | Magnesium carbonate | 0.140 | 0.140 | 0.140 | 0.140 | 0.140 |
| | Phosphate | 0.3 | 0.3 | 0.3 | 0.3 | 0.3 |
| | Other minerals | 0.260 | 0.260 | 0.260 | 0.260 | 0.260 |

TABLE 3-continued

| Component composition (unit: g) | | Example 3 | Example 4 | Comparative Example 3 | Comparative Example 4 | Comparative Example 5 |
|---|---|---|---|---|---|---|
| Plant protein | Soybean protein | 4.4 | 4.4 | 4.4 | 4.4 | 4.4 |
| Emulsifier | Lysolecithin | 0.34 | — | — | — | — |
| | Sucrose laurate | — | 0.34 | — | — | — |
| | Lecithin | — | — | 0.34 | — | — |
| | Diacetyl tartrate | — | — | — | 0.34 | — |
| | Hexaglycerol tristearate | — | — | — | — | 0.34 |
| Fat | Corn oil | 3.4 | 3.4 | 3.4 | 3.4 | 3.4 |
| Carbohydrate | Dextrin | 12.0 | 12.0 | 12.0 | 12.0 | 12.0 |
| Vitamins | Vitamin premix | 0.170 | 0.170 | 0.170 | 0.170 | 0.170 |
| Dietary fiber | Dietary fiber | 1.2 | 1.2 | 1.2 | 1.2 | 1.2 |
| Distilled water | | Balance | Balance | Balance | Balance | Balance |
| Total (volume) | | 100 ml | 100 ml | 100 ml | 100 ml | 100 ml |

TABLE 4

| Evaluation | Example 3 | Example 4 | Comparative Example 3 | Comparative Example 4 | Comparative Example 5 |
|---|---|---|---|---|---|
| Solidification ratio (%) | 51 | 46 | 36 | 41 | 44 |
| Aggregate (g) | 0.01 | 0.07 | 0.3 | 0.14 | 0.13 |
| Viscosity (cP) | 77 | 161 | 190 | 182 | 185 |
| Granular texture | Absence | Absence | Presence | Presence | Presence |
| Easiness in intake | A | B | C | C | C |

(Passage Performance Evaluation in Tube Administration)

Using the liquid food compositions prepared in Examples 3 and 4 and Comparative Example 3, the passage performance of each of the liquid food composition at the time of tube administration was examined.

The tube used for the examination was a general purpose tube for enteral nutrient that had a tube size of 16 Fr and a tube length of 135 cm and equipped with a speed control throttle at a distance of 30 cm from an end of the tube. For the examination, a liquid food composition was transferred to a plastic bottle (JMS feeding bottle), then the plastic bottle was placed so that the lower end of the bottle was positioned at a height of 150 cm from a floor, and an end of the tube was connected to the lower end of the plastic bottle. In addition, the tube end opposite to the end connected to the plastic bottle was placed at a height of 50 cm from the floor. In the examination, the speed control throttle of the tube was adjusted so that distilled water would flow at a flow speed of 200 g/minute, then each liquid food composition flowed, and the passage performance was observed.

Figure 7:
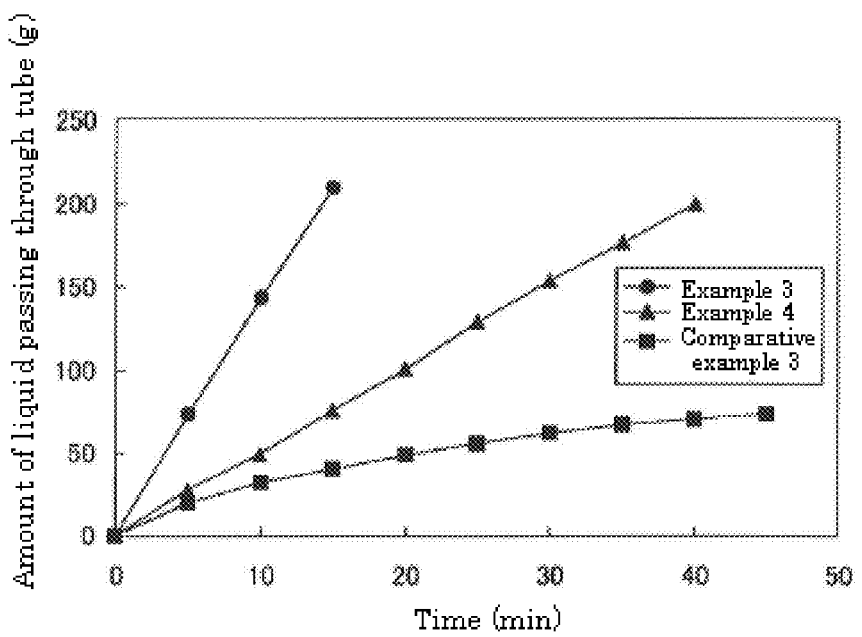
FIG. 7 is a figure showing the time course of the amount of liquid passing through a tube when each liquid food composition prepared in Examples 3 and 4 and Comparative Example 3 was subjected to passage performance evaluation on tube feeding.

The results are shown in FIG. 7. The composition containing lysolecithin caused little aggregate clogging and had very good tube passage performance. The liquid food composition containing sucrose laurate caused little aggregate clogging and had good tube passage performance. As described above, the composition containing lysolecithin or sucrose laurate could be suitably used for tube administration. However, the composition containing lecithin caused aggregate clogging, had poor tube passage performance, and finally did not flow. As described above, the liquid food composition containing lecithin could not be used for tube administration.

(Dependency Evaluation on Amount of Emulsifier Added)

Liquid food compositions were prepared in a similar manner to that in Example 1 except that lysolecithin was used as an emulsifier in various amounts (mixing ratio of emulsifier/fat based on weight) as shown in Table 5. In the composition in Example 1, the amount of fat added was kept constant and the amount of the emulsifier was changed. The prepared liquid food compositions A to E were subjected to the same evaluation as the above. The evaluation results are shown in Table 5.

Each of the liquid food compositions A and B had a solidification ratio of 41% or less, an aggregate weight of 0.13 g or more, and a viscosity of 158 cP or more. Comparing with the liquid food compositions C to E, each composition had a lower solidification ratio and was liquid but in a non-uniform state, for example, the aggregates were visually observed, and also each composition had a high viscosity. The particle size distributions of particles in the liquid food compositions A and B were shown in FIGS. 8(a) and 9(a), respectively. Each particle size distribution of the liquid food compositions A and B had a peak in a section having a particle size of 3,000 nm or larger. The ultrasonic treatment reduced the frequency of the peak but no peak was observed in a section having a particle size of 3,000 nm or smaller.

Figure 8:
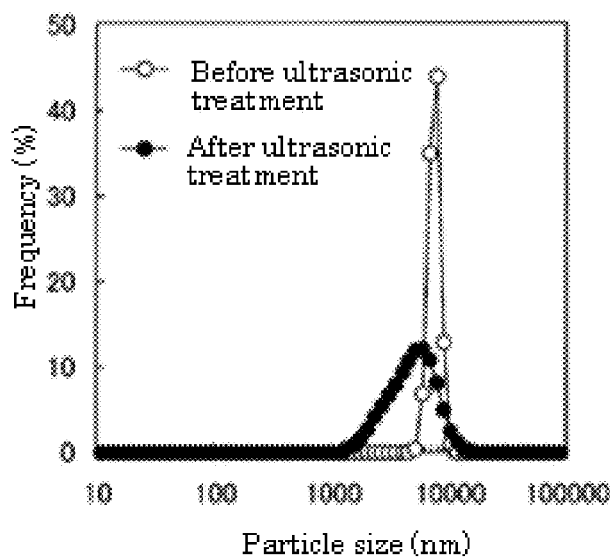
FIG. 8($a$) is a figure showing the particle size distribution of particles in a liquid food composition A in a dependency evaluation on the amount of an emulsifier added and FIG. 8($b$) is a figure showing the particle size distribution of particles in the liquid food composition A as a distribution curve where vertical axis is passing particle integrated value (%) based on volume.
Figure 8:
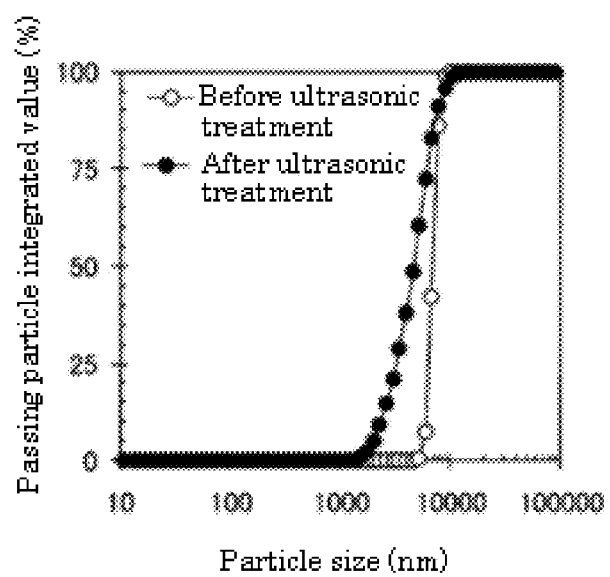
Figure 9:
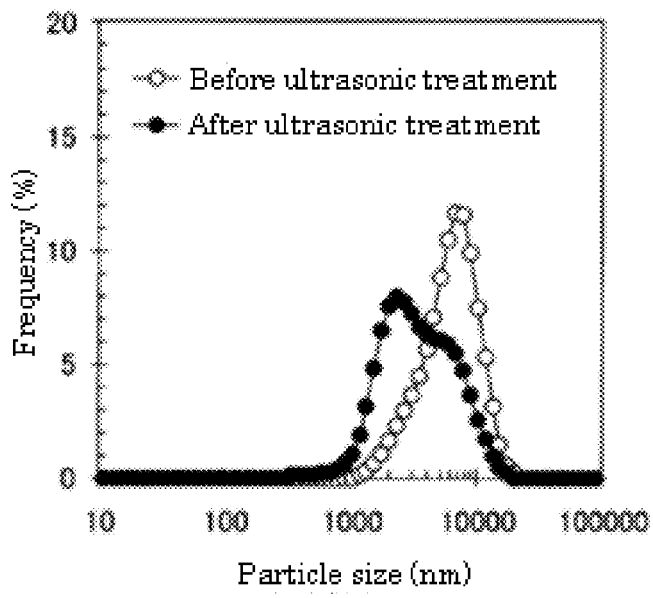
FIG. 9($a$) is a figure showing the particle size distribution of particles in a liquid food composition B in the dependency evaluation on the amount of an emulsifier added and FIG. 9($b$) is a figure showing the particle size distribution of particles in the liquid food composition B as a distribution curve where vertical axis is passing particle integrated value (%) based on volume.
Figure 9:
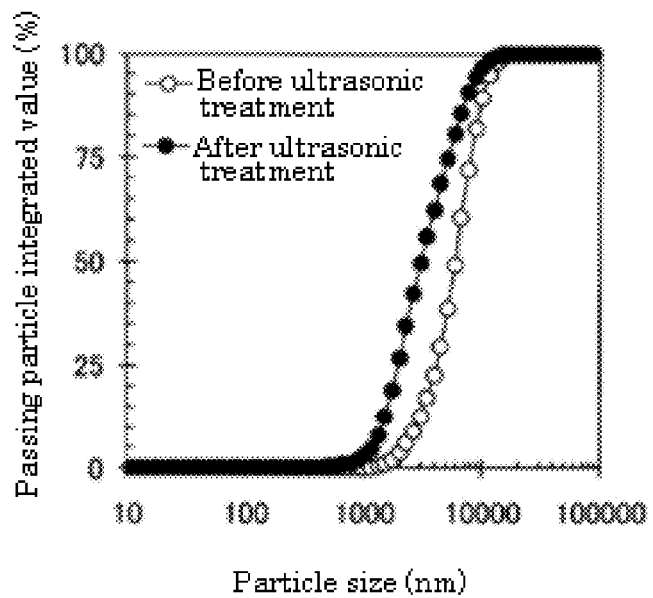

The particle size distributions of the liquid food compositions A and B are represented as distribution curves where the vertical axis is passing particle integrated value (%) based on volume, and shown in FIGS. 8(b) and 9(b). The particle size distribution curve had only one inflection point in each of the compositions A and B. Each liquid food composition had granular texture and poor flowability at the time of oral intake and was difficult to be taken.

Figure 10:
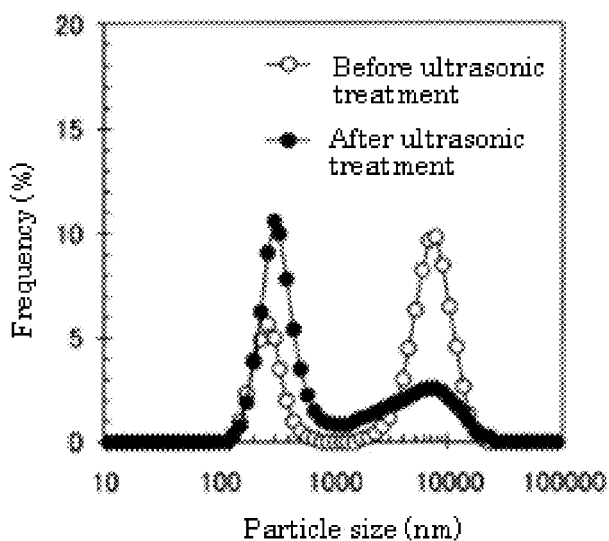
FIG. 10($a$) is a figure showing the particle size distribution of particles in a liquid food composition C in the dependency evaluation on the amount of an emulsifier added and FIG. 10($b$) is a figure showing the particle size distribution of particles in the liquid food composition C as a distribution curve where vertical axis is passing particle integrated value (%) based on volume.
Figure 10:
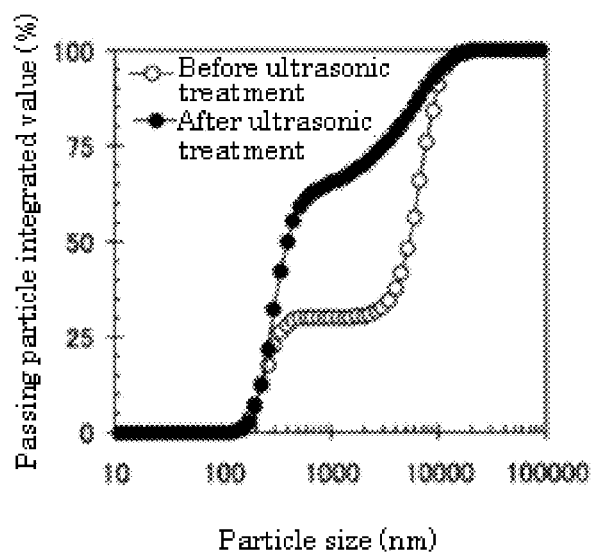
Figure 11:
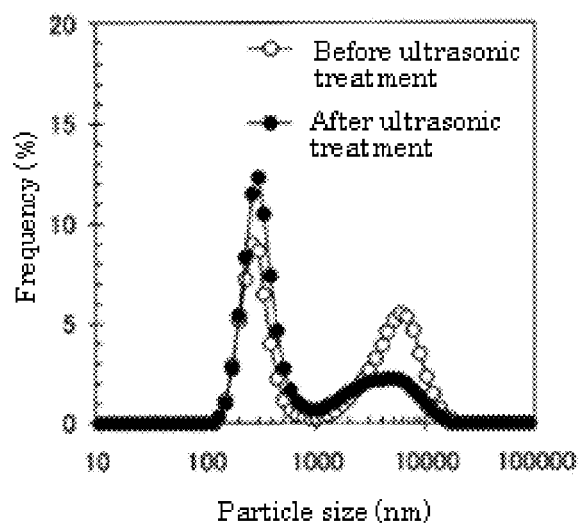
FIG. 11($a$) is a figure showing the particle size distribution of particles in a liquid food composition D in the dependency evaluation on the amount of an emulsifier added and FIG. 11($b$) is a figure showing the particle size distribution of particles in the liquid food composition D as a distribution curve where vertical axis is passing particle integrated value (%) based on volume.
Figure 11:
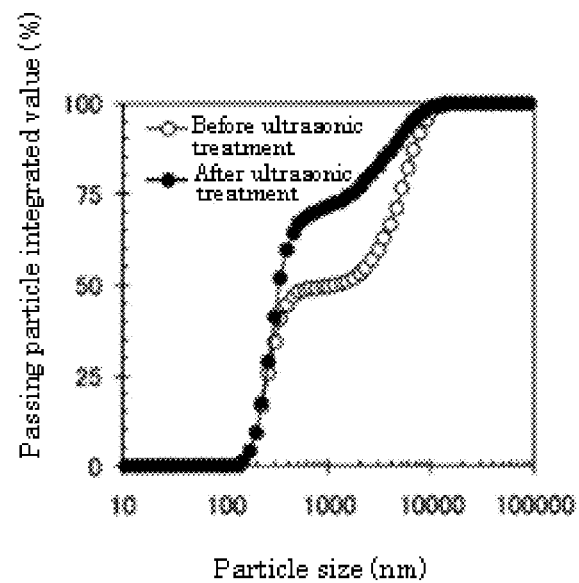
Figure 12:
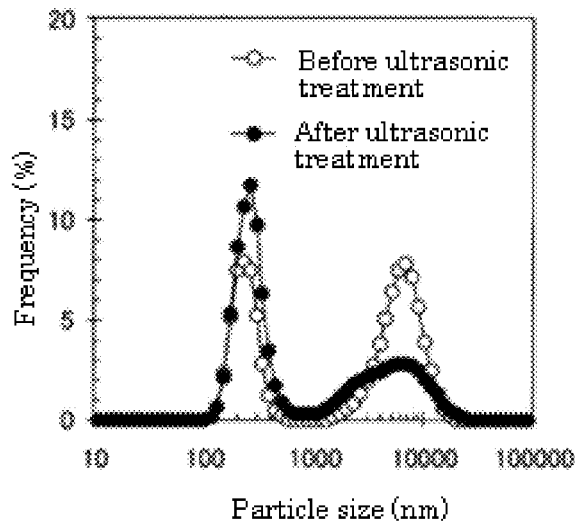
FIG. 12($a$) is a figure showing the particle size distribution of particles in a liquid food composition E in the dependency evaluation on the amount of an emulsifier added and FIG. 12($b$) is a figure showing the particle size distribution of particles in the liquid food composition E as a distribution curve where vertical axis is passing particle integrated value (%) based on volume.
Figure 12:
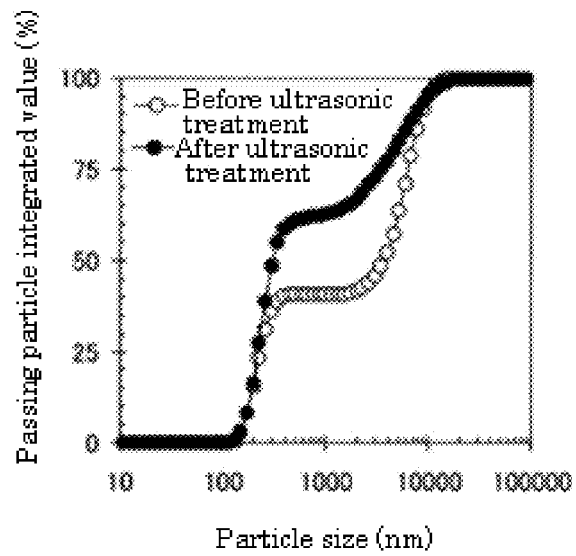

The liquid food compositions C to E were uniform liquids and the generation of solids and the separation of nutrient components were not observed. The solidification ratio was 49% or more, the aggregate weight was 0.03 g or less, and the viscosity was 133 cP or less. The particle size distributions of particles in the liquid food compositions C to E are shown in FIG. 10(a), FIG. 11(a), and FIG. 12(a), respectively. Each particle size distribution of the liquid food compositions C to E had two peaks, and the smaller peak was present in a section having a particle size of 3,000 nm or smaller. The ultrasonic treatment reduced the frequency of the larger peak and increased the frequency of the smaller peak present in the section having a particle size of 3,000 nm or smaller. Evaluating each peak frequency increased or reduced before and after the ultrasonic treatment by the aforementioned equation, in the liquid food composition C, the smaller peak having the increased peak frequency was 190% (=10.569%/5.618%×100), while the larger peak having the reduced peak frequency was 26% (=2.550%/9.755%×100). In the liquid food composition D, the smaller peak having the increased peak frequency was 140% (=12.32%/8.999%×100), while the larger peak having the reduced peak frequency was 40% (=2.188%/5.482%×100). In the liquid food composition E, the smaller peak having the increased peak frequency was 150% (=11.676%/7.871%×100), while the larger peak having the reduced peak frequency was 36% (=2.819%/7.764%×100).

The particle size distributions of the liquid food compositions C to E are represented as distribution curves where the vertical axis is passing particle integrated value (%) based on volume, and shown in FIG. 10(b), FIG. 11(b), and FIG. 12(b). In each of the compositions C to E, the particle size distribution curve had three inflection points, in C, of (1) at a passing particle integrated value of around 12.27% and a particle size of around 226 nm, of (2) at around 30.12% and around 1,005 nm, and of (3) at around 66.19% and around 6,720 nm, in D, of (4) at around 16.58% and around 226 nm, of (5) at around 49.19% and around 766 nm, and of (6) at around 76.27% and around 5,122 nm, and, in E, of (7) at around 15.63% and around 197 nm, of (8) at around 40.82% and around 766 nm, and of (9) at around 71.13% and around 5,867 nm. The ultrasonic treatment shifted the inflection points (2, 5, and 8) of the compositions C to E, in C, to (2') at around 64.58% and around 877 nm, in D, to (5') at around 70.79% and around 877 nm, and in E, to (8') at around 62.08% and around 766 nm after the ultrasonic treatment, and the variations of the passing particle integrated values were 34% increase in C, 22% increase in D, and 21% increase in E as compared with those before the ultrasonic treatment.

Each composition had less granular texture and good swallowing feeling at the time of oral intake and was readily taken.

Figure 15:
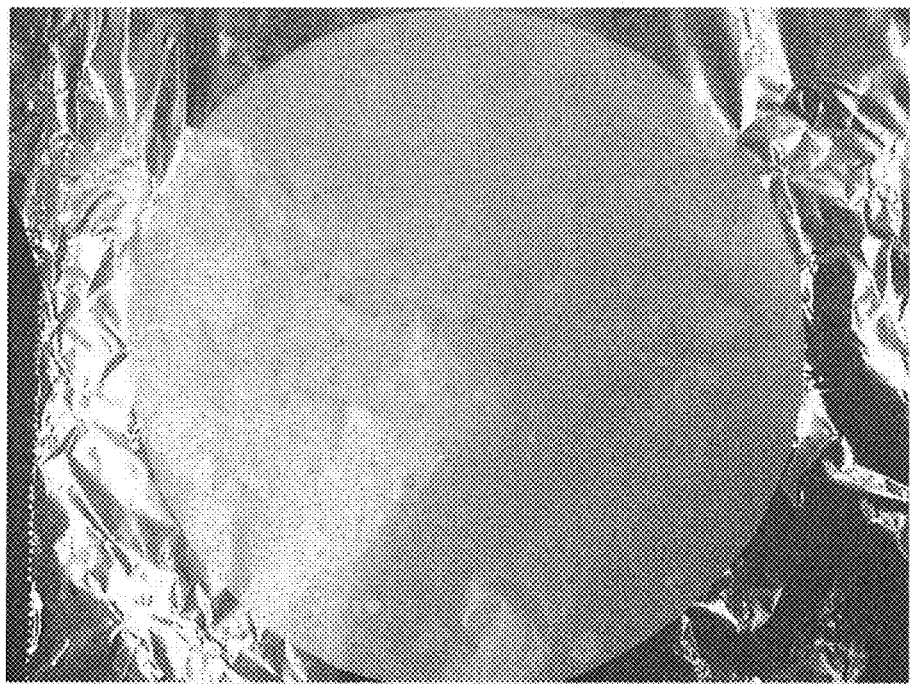
FIG. 15 is a figure showing the generation state of aggregates as a residue after the liquid food composition D was filtered in the dependency evaluation on the amount of an emulsifier added.
Figure 16:
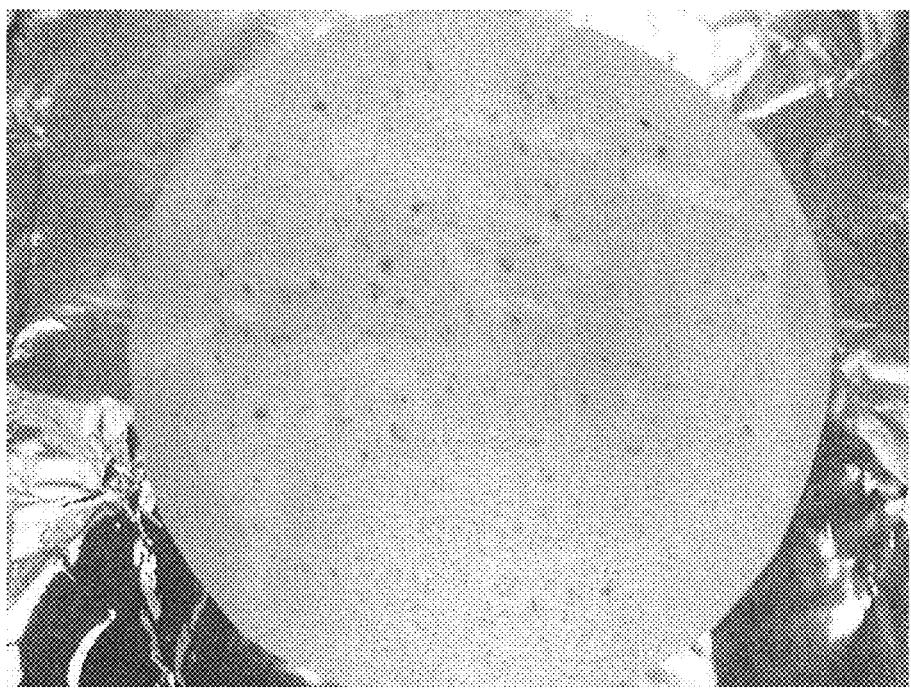
FIG. 16 is a figure showing the generation state of aggregates as a residue after the liquid food composition E was filtered in the dependency evaluation on the amount of an emulsifier added.

In a similar manner to the weighing of the aggregates, the liquid compositions D and E were filtered and the generations of aggregates as the residue were shown in FIGS. 15 and 16, respectively. In the liquid compositions D and E, the dotted dark parts are aggregates, but few dark parts were observed on the nylon screen, and it is clear that the generation of aggregates was effectively suppressed.

TABLE 5

| | Liquid food composition | | | | |
|---|---|---|---|---|---|
| | A | B | C | D | E |
| Mixing ratio of emulsifier/fat | 1/100 | 5/100 | 7/100 | 10/100 | 20/100 |
| Solidification ratio (%) | 40 | 41 | 49 | 51 | 51 |
| Aggregate (g) | 0.194 | 0.131 | 0.03 | 0.009 | 0.016 |
| Viscosity (cP) | 158 | 165 | 133 | 77 | 85 |
| Change in particle size distribution | Not changed | Not changed | Changed | Changed | Changed |
| Granular texture | Presence | Presence | Absence | Absence | Absence |
| Easiness in intake | B | B | A | A | A |

(Viscosity Measurement of Liquid Food Composition after Semi-Solidification)

Based on the formulation described in Table 6, a liquid food composition was prepared.

To 650 ml of distilled water, 10 g of sodium alginate was added. Next, a dextrin powder and a soybean protein powder were sequentially added and a fat (containing an emulsifier) was further added. Then, calcium carbonate, magnesium carbonate, a phosphate, a potassium salt, a sodium salt, other minerals, and vitamins were added, and the whole was stirred. The other minerals used were a mixture of a zinc-containing yeast, a copper-containing yeast, a manganese-containing yeast, a chromium-containing yeast, a selenium-containing yeast, a molybdenum-containing yeast (these mineral-containing yeasts: manufactured by Medience Corporation), and ferric sodium citrate (manufactured by Ebisu Co., Ltd). Then, distilled water was added to make the volume 1,000 ml and the mixture was homogenized with a Manton Gaulin high-pressure emulsification equipment (Rannie 2000: manufactured by APV) (for the first time: 20 MPa, for the second time: 48 MPa). Each soft bag (R1420H: manufactured by Meiwa Pax Co., Ltd.) were filled with 200 g of the prepared liquid food composition, and the whole was sterilized (121° C., 20 minutes) in an autoclave sterilizer. The liquid food composition had a pH of 6.7 before pH adjustment.

Viscosity was determined with a Brookfield viscometer. Into a glass container having an inner diameter of 60 mm, 200 ml of the liquid food composition was charged, the pH of the composition was adjusted to a pH of 4.5 to 5.5 using 5N HCl (extremely gently stirred for preventing a solidified product from being destroyed), and the composition was left for 5 minutes. After the standing, the measurement was carried out in a condition at a rotation speed of 12 revolutions per minute and a holding time of 1 minute to read a measured value. The rotor type was properly changed as shown in Table 7 depending on the viscosity of a sample.

The measured results are shown in Table 7. As shown in Table 7, the liquid food composition had an increased viscosity of 1,000 cP or more in an acidic region. In particular, at a pH of 4.5, the viscosity was increased to 10,000 cP or more.

TABLE 6

| Component | | Formulation [g] |
|---|---|---|
| Water-soluble dietary fiber | Sodium alginate | 1.0 |
| Minerals | Calcium carbonate | 0.180 |
| | Magnesium carbonate | 0.140 |
| | Phosphate | 0.6 |
| | Potassium salt | 0.440 |
| | Sodium salt | 0.170 |
| | Other minerals | 0.062 |
| Plant protein | Soybean protein | 4.4 |
| Emulsifier | Lysolecithin | 0.34 |
| Fat | Corn oil | 3.4 |
| Carbohydrate | Dextrin | 12.0 |
| Vitamins | Vitamin premix | 0.060 |
| Dietary fiber | Dietary fiber | 3.8 |
| Distilled water | | Balance |
| Total (volume) | | 100 ml |

TABLE 7

| pH at the time of preparation | Rotor No. | Viscosity (cP) |
|---|---|---|
| 5.5 | 2 | 1260 |
| 5.0 | 3 | 8950 |
| 4.5 | 4 | 10,000 or more |

The invention claimed is:

1. A liquid food composition, comprising:
0.3 wt % to 5.0 wt % of a water-soluble dietary fiber (a);
a metal compound (b) containing a necessary mineral component for humans and not causing gelation of the water-soluble dietary fiber at a pH of 5.5 to 10.0;
a protein (c); and
an emulsifier (d),
wherein the liquid food composition is semi-solidified at a pH of 5.5 or less,
wherein particles in the liquid food composition have a particle size distribution with two or more peaks at the pH of 5.5 to 10.0, wherein a first peak of the two or more peaks in the particle size distribution is at a particle size of 3,000 nm or smaller, wherein a second peak of the two or more peaks in the particle size distribution has an inflection point at a particle size of about 10,000 nm, wherein a curvature of a curve in the particle size distribution is positive from a particle size of about 3,400 nm to the particle size of about 10,000 nm, and wherein the curvature of the curve in the particle size distribution is negative at a particle size of about 10,000 nm or higher.

2. The liquid food composition according to claim 1, wherein the liquid food composition in a semi-solidified state has a viscosity of 1,000 cP or more at the pH of 5.5 or less.

3. The liquid food composition according to claim 1,
wherein a frequency of the first peak at the particle size of 3,000 nm or smaller is increased after an ultrasonic treatment of the liquid food composition, as compared with a frequency of the first peak before the ultrasonic treatment, and wherein a frequency of the second peak is reduced after the ultrasonic treatment, as compared with a frequency of the second peak before the ultrasonic treatment.

4. The liquid food composition according to claim 3,
wherein in the first peak having the increased frequency after the ultrasonic treatment, the increased frequency is 105% or more with respect to the frequency of the first peak before the ultrasonic treatment, and wherein in the second peak having the reduced frequency after the ultrasonic treatment, the reduced frequency is 60% or less with respect to the frequency of the second peak before the ultrasonic treatment.

5. The liquid food composition according to claim 1,
wherein an aggregate weight of the liquid food composition is 0.1 g or less, the aggregate weight being measured by weighing a first dry weight (W1) of a 264-mesh nylon screen; filtering 200 ml of the liquid food composition using the 264-mesh nylon screen; drying the 264-mesh nylon screen at 60° C. for 1 hour after the filtering step and then cooling the 264-mesh nylon screen; weighing a second dry weight (W2) of the 264-mesh nylon screen; and calculating a difference (W2−W1) between the first dry weight (W1) and the second dry weight (W2) to determine weight of an aggregate of the liquid food composition obtained as a residue.

6. The liquid food composition according to claim 1,
wherein the water-soluble dietary fiber (a) is alginic acid and/or a salt thereof.

7. The liquid food composition according to claim 1,
wherein the protein (c) is a plant protein derived from a plant.

8. The liquid food composition according to claim 7,
wherein the plant protein is a bean-derived protein.

9. The liquid food composition according to claim 8,
wherein the bean-derived protein is a soybean protein and/or a hydrolysate thereof.

10. The liquid food composition according to claim 1,
wherein the metal compound (b) is at least one compound selected from the group consisting of a metal compound having poor solubility at the pH of 5.5 to 10.0, a metal compound included in a microorganism such as a yeast, and a metal compound included in a microcapsule.

11. The liquid food composition according to claim 10,
wherein the metal compound (b) is a calcium compound having poor solubility at the pH of 5.5 to 10.0 and/or a magnesium compound having poor solubility at the pH of 5.5 to 10.0.

12. The liquid food composition according to claim 11,
wherein the metal compound (b) is the calcium compound having poor solubility at the pH of 5.5 to 10.0, and wherein the calcium compound is at least one compound selected from the group consisting of calcium citrate, calcium carbonate, calcium dihydrogen pyrophosphate, tricalcium phosphate, calcium monohydrogen phosphate, calcium stearate, and calcium silicate.

13. The liquid food composition according to claim 11,
wherein the metal compound (b) is the magnesium compound having poor solubility at the pH of 5.5 to 10.0, and wherein the magnesium compound is at least one compound selected from the group consisting of magnesium carbonate, magnesium oxide, magnesium stearate, and trimagnesium phosphate.

14. The liquid food composition according to claim 10,
wherein the metal compound (b) is at least one selected from the group consisting of a zinc-containing yeast, a copper-containing yeast, a manganese-containing yeast, a chromium-containing yeast, a selenium-containing yeast, and a molybdenum-containing yeast.

15. The liquid food composition according to claim 10,
wherein the metal compound (b) is ferric sodium citrate.

16. The liquid food composition according to claim 1,
wherein the emulsifier (d) is an emulsifier having an HLB value of more than 9.

17. The liquid food composition according to claim 16,
wherein the emulsifier (d) is lysolecithin and/or a sucrose fatty acid ester that comprises a fatty acid monoester having a carbon number of 18 or less.

18. The liquid food composition according to claim 16,
wherein the emulsifier (d) is lysolecithin and/or sucrose laurate.

19. The liquid food composition according to claim 1,
further comprising a fat (e).

20. The liquid crystal food composition according to claim 19,
wherein the emulsifier (d) and the fat (e) are mixed in a ratio ((d)/(e), based on weight) of more than 5/100 and less than 30/100.

21. The liquid food composition according to claim 1,
wherein at least the components (a) to (d) are filled in a container as a one-pack type product.

22. The liquid food composition according to claim 1,
further comprising a nutrient component (f).

23. The liquid food composition according to claim 1,
wherein the liquid food composition is in a liquid state.

24. An enteral nutrition food comprising the liquid food composition according to claim 1.

25. An oral nutrition food comprising the liquid food composition according to claim 1.

26. A diet food comprising the liquid food composition according to claim 1.

* * * * *